US010815478B2

(12) United States Patent
Gloeckner et al.

(10) Patent No.: US 10,815,478 B2
(45) Date of Patent: Oct. 27, 2020

(54) METHOD OF SEQUENTIAL TAGMENTATION WITH TRANSPOSASE COMPOSITIONS FOR REDUCTION OF INSERTION BIAS

(71) Applicant: Illumina, Inc., San Diego, CA (US)

(72) Inventors: Christian Gloeckner, Bonn (DE); Amirali Kia, San Diego, CA (US); Molly He, San Diego, CA (US); Trina Faye Osothprarop, San Diego, CA (US); Frank J. Steemers, Encinitas, CA (US); Kevin L. Gunderson, Encinitas, CA (US); Sasan Amini, Redwood City, CA (US); Jerome Jendrisak, Madison, WI (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 15/523,765

(22) PCT Filed: Nov. 5, 2015

(86) PCT No.: PCT/US2015/059194
§ 371 (c)(1),
(2) Date: May 2, 2017

(87) PCT Pub. No.: WO2016/073690
PCT Pub. Date: May 12, 2016

(65) Prior Publication Data
US 2018/0016571 A1 Jan. 18, 2018

Related U.S. Application Data

(60) Provisional application No. 62/242,935, filed on Oct. 16, 2015, provisional application No. 62/075,713, filed on Nov. 5, 2014.

(51) Int. Cl.
*C12N 15/10* (2006.01)
*C12N 9/12* (2006.01)

(52) U.S. Cl.
CPC ....... *C12N 15/1065* (2013.01); *C12N 9/1241* (2013.01); *C12N 15/1093* (2013.01); *C12Y 207/07* (2013.01)

(58) Field of Classification Search
CPC .................. C12N 15/1065; C12N 15/1082
See application file for complete search history.

(56) References Cited

U.S. PATENT DOCUMENTS

| | | | | |
|---|---|---|---|---|
| 6,593,113 B1 * | 7/2003 | Tenkanen | ............. | C12Q 1/6869 435/6.16 |
| 9,683,230 B2 * | 6/2017 | Gormley | ............. | C12N 15/1065 |
| 2010/0120098 A1 | 5/2010 | Grunenwald | | |
| 2012/0301925 A1 | 11/2012 | Belyaev | | |
| 2014/0093916 A1 | 4/2014 | Belysver | | |
| 2014/0194324 A1 * | 7/2014 | Gormley | ............. | C12Q 1/6869 506/17 |
| 2015/0284714 A1 * | 10/2015 | Gormley | ............. | C12Q 1/6869 506/16 |
| 2015/0291942 A1 * | 10/2015 | Gloeckner | ........... | C12N 9/1241 506/2 |

FOREIGN PATENT DOCUMENTS

| | | | | |
|---|---|---|---|---|
| EP | 2527438 | | 11/2012 | |
| EP | 2712931 | | 4/2014 | |
| FR | 2900935 | | 11/2007 | |
| WO | WO 1995/23875 | | 9/1995 | |
| WO | WO 2010/048605 | | 4/2010 | |
| WO | WO 2014/108810 | | 7/2014 | |
| WO | WO-2014205296 A1 * | 12/2014 | ........... C12Q 1/6806 |
| WO | WO-2015089339 A2 * | 6/2015 | ......... C12N 15/1093 |
| WO | WO-2016073690 A1 * | 5/2016 | ......... C12N 15/1093 |

OTHER PUBLICATIONS

Green et al. Insertion site preference of Mu, Tn5, and Tn7 transposons. Mobile DNA, vol. 3, 3, 2012, printed as pp. 1/6-6/6. (Year: 2012).*
Crenes et al. The bacterial Tn9 chloramphenicol resistance gene: an attractive DNA segment for Mos1 mariner insertions. Molecular Genetics and Genomics: MGG, vol. 281, No. 3, pp. 315-325, 2009, Epub Dec. 27, 2008. (Year: 2008).*
Saariaho et al. Characteristics of MuA transposase-catalyzed processing of model transposon end DNA hairpin substrates. Nucleic Acids Research, vol. 34, No. 10, pp. 3139-3149, Jun. 6, 2006. (Year: 2006).*
Gangadharan et al. DNA transposon Hermes insertes into DNA in nucleosome-free regions in vivo. Proceedings of the National Academy of Sciences, USA, vol. 107, No. 51, pp. 21966-21972, Dec. 3, 2010, including pp. 1/6-6/6 of Supporting Information. (Year: 2010).*
Biery et al. A simple in vitro Tn7-based transposition system with low target site selectivity for genome and gene analysis. Nucleic Acids Research, vol. 28, No. 5, pp. 1067-1077, 2000. (Year: 2000).*
Hickman et al. Structural basis of hAT transposon end recognition by Hermes, an octameric DNA transosase from *Musca domestica*. Cell, vol. 158, pp. 353-367, Jul. 2014, including pp. S1-S14 of Supplemental Information. (Year: 2014).*
Boeke & Corces, Transcription and Reverse Transcription of Retrotransposons, Annu Rev Microbiol. 43:403-34 (1989).
Brown, et al., Retroviral integration: Structure of the initial covalent product and its precursor, and a role for the viral IN protein, Proc Natl Acad Sci USA 86:2525-9 (1989).
Colegio et al., In Vitro Transposition System for Efficient Generation of Random Mutants of Campylobacter, J. Bacteriol. 183: 2384-8 (2001).

(Continued)

*Primary Examiner* — Jennifer Dunston
(74) *Attorney, Agent, or Firm* — Knobbe, Martens, Olson & Bear LLP

(57) ABSTRACT

Presented herein are methods and compositions for tagmentation of nucleic acids. The methods are useful for generating tagged DNA fragments that are qualitatively and quantitatively representative of the target nucleic acids in the sample from which they are generated.

14 Claims, 28 Drawing Sheets

Specification includes a Sequence Listing.

(56) References Cited

OTHER PUBLICATIONS

Craig, N L, Transposon Tn7, Review in: Curr Top Microbiol Immunol., 204:27-48 (1996).
Craig, N L, V(D)J Recombination and Transposition: Closer than Expected, Science. 271: 1512 (1996).
DeMattei et al, Site-directed integration of transgenes: transposons revisited using DNA-binding-domain technologies, Genetica; An International Journal of Genetics and Evolution, 138(5):531-540 (2009).
Devine & Boeke, Efficient integration of artificial transposons into plasmid targets in vitro: a useful tool for DNA mapping, sequencing and genetic analysis, Nucleic Acids Res. 22:3765-72 (1994).
Gloor, G B, Gene Targeting in Drosophila, Methods Mol. Biol. 260: 97-114 (2004).
Goryshin and Reznikoff, Tn5 in Vitro Transposition, J. Biol. Chem. 273:7367 (1998).
Ichikawa & Ohtsubo, In Vitro Transposition of Transposon Tn3*, J Biol. Chem. 265:18829-32 (1990).
Kirby C et al., Cryptic plasmids of *Mycobacterium avium*: Tn552 to the rescue, Mol. Microbiol., 43: 173-86 (2002).
Kleckner N, et al., Tn10 and IS10 Transposition and Chromosome Rearrangements: Mechanism and Regulation In Vivo and In Vitro, Curr Top Microbiol Immunol., 204:49-82 (1996).
Kozarewa, et al, Amplification-free Illumina sequencing-library preparation facilitates improved mapping and assembly of (G+C)-biased genomes, Nature Methods 6(4):291-295 (2009).
Lampe, et al., A purified mariner transposase is sufficient to mediate transposition in vitro, EMBO J., 15: 5470-9 (1996).
Mizuuchi, K., In Vitro Transposition of Bacteriophage Mu: A Biochemical Approach to a Novel Replication Reaction, Cell, 35: 785 (1983).
Naumann, et al, Production of combinatorial libraries of fused genes by sequential transposition reactions, Nucleic Acids Research, 30(21):e119-1 (2002).
Ohtsubo & Sekine, Bacterial Insertion Sequences, Curr. Top. Microbiol. Immunol. 204: 1-26 (1996).
Plasterk R H, The Tc1/mariner Transposon Family, Curr. Topics Microbiol. Immunol. 204: 125-43 (1996).
Savilahti, et al. The phage Mu transpososome core: DNA requirements for assembly and function, EMBO J., 14: 4893 (1995).
Wilson C. et al., New transposon delivery plasmids for insertional mutagenesis in Bacillus anthracis, J. Microbiol. Methods 71:332-5 (2007).
Zhang et al., A novel mechanism of transposon-mediated gene activation, PLoS Genet. 5:e1000689. Epub Oct. 16, 2009 (2009).
Picelli S. et al, Tn5 transposase and tagmentation procedures for massively-scaled sequencing projects, Genome Research 24: 2033-2040 (2014).

* cited by examiner

Oligo Sequences Used for Mu Tsm

MM1141:
TGTTTTCGCATTTATCGTGAACGCTTTCGCGTTTTTCGTGCGCCGCTTCA

MM1138:
TCGGATGAAGCGGGCGCACGAAAAACGCGAAAGCGTTTCACGATAAATGCGAAAACA

```
MM1141  1    TGTTTTCGCATTTATCGTGAAACGCTTTCGCGTTTTTCGTGCGCCGCTTCA   51
             ||||||||||||||||||||||||||||||||||||||||||||||||||
MM1138  56   TGTTTTCGCATTTATCGTGAAACGCTTTCGCGTTTTTCGTGCGCCGCTTCA   6
```

Sequencing Primer (MuPCRts):
CGTTTTTCGTGCGCCGCTTCA

P7MUTS:
CAAGCAGAAGACGGCATACGAGATCGTTTTTCGTGCGCCGCTTCA

P5MUTS:
AATGATACGGCGACCACCGAGATCTACACCGTTTTTCGTGCGCCGCTTCA

Figure 16

Some Statistics of the Sequencing Run

| | |
|---|---|
| total # of reads | 30,078,951 |
| # of reads pass eland alignment | 16,775,955 |
| # of unique reads | 4,629,392 |
| # of unique reads <2000bp | 4,599,874 |
| mean coverage | 69.39X |

Figure 19

SEQUENCE LISTING

<160> NUMBER OF SEQ ID NOS: 5

<210> SEQ ID NO 1
<211> LENGTH: 51
<212> TYPE: DNA
<213> ORGANISM: Artificial Sequence
<220> FEATURE:
<223> OTHER INFORMATION: HyperMu transposon sequence

<400> SEQUENCE: 1
tgttttcgca tttatcgtga aacgctttcg cgttttcgt gcgccgcttc a    51

<210> SEQ ID NO 2
<211> LENGTH: 56
<212> TYPE: DNA
<213> ORGANISM: Artificial Sequence
<220> FEATURE:
<223> OTHER INFORMATION: HyperMu transposon sequence

<400> SEQUENCE: 2
tcggatgaag cggcgcacga aaaacgcgaa agcgtttcac gataaatgcg aaaaca    56

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3 cgttttcgt gcgccgcttc a    21

<210> SEQ ID NO 4
<211> LENGTH: 44
<212> TYPE: DNA
<213> ORGANISM: Artificial Sequence
<220> FEATURE:
<223> OTHER INFORMATION: Primer

<400> SEQUENCE: 4
caagcagmga cggcatacga gatcgttttt cgtgcgccgc ttca    44

-continued

```
<210> SEQ ID NO 5
<211> LENGTH: 50
<212> TYPE: DNA
<213> ORGANISM: Artificial Sequence
<220> FEATURE:
<223> OTHER INFORMATION: Primer

<400> SEQUENCE: 5
aatgatacgg cgaccaccga gatctacacc gtttttcgtg cgccgcttca            50
```

METHOD OF SEQUENTIAL TAGMENTATION WITH TRANSPOSASE COMPOSITIONS FOR REDUCTION OF INSERTION BIAS

RELATED APPLICATIONS

This application is the U.S. national phase of PCT/US2015/059194 filed Nov. 5, 2015 and published in English as WO 2016/073690 on May 12, 2016 which claims priority to U.S. provisional application Nos.: 62/075,713 filed on Nov. 5, 2014 and 62/242,935 filed on Oct. 16, 2015, which are each hereby incorporated by reference in its entirety.

REFERENCE TO SEQUENCE LISTING

The present application includes a Sequence Listing in electronic format. The Sequence Listing is provided as a file entitled ILLINC385NPSEQLISTING.TXT, created Sep. 28, 2017, which is approximately 1.5 Kb in size. The information in the electronic format of the Sequence Listing is incorporated herein by reference in its entirety.

BACKGROUND

Transposase enzymes are useful in in vitro transposition systems. They allow for massive-scale fragmentation and tagging of genomic DNA and are useful for making libraries of tagged DNA fragments from target DNA for use in nucleic acid analysis methods such as next-generation sequencing and amplification methods. There remains a need for transposase compositions and tagmentation methods with improved properties and which generate tagged DNA fragments that are qualitatively and quantitatively representative of the target nucleic acids in the sample from which they are generated.

BRIEF SUMMARY

Presented herein are methods and compositions for tagmentation of nucleic acids. The transposase compositions and tagmentation methods provided herein have surprisingly improved properties including, for example, generating tagged DNA fragments that are qualitatively and quantitatively representative of the target nucleic acids in the sample from which they are generated.

Accordingly, one embodiment presented herein is a method of sequential tagmentation comprising: (a) providing a first transposome, the first transposome comprising a first transposase enzyme having a first tagmentation profile; (b) combining a target nucleic acid with the first transposase enzyme under conditions suitable for tagmentation, thereby generating a tagmented nucleic acid; (c) combining the tagmented nucleic acid with a second transposome under conditions suitable for tagmentation, the transposome comprising a second transposase enzyme having a tagmentation profile. In some embodiments, the first tagmentation profile and the second tagmentation profile are different. In some embodiments, the method comprises a wash step between steps (b) and (c) to substantially separate the tagmented nucleic from reaction buffer used in step (b). In some embodiments, the wash step comprises binding the tagmented nucleic acid to a solid support. In some embodiments, the solid support comprises beads. In some embodiments, the solid support comprises a spin column. In some embodiments, the first transposome and the second transposome have different insertion bias. In some embodiments, step (c) comprises adding the second transposome to a reaction mixture comprising the first transposome.

Also presented herein is method of tagmentation comprising: (a) providing a first transposome, the first transposome comprising a first transposase enzyme having a first tagmentation profile; (b) providing a second transposome, the second transposome comprising a second transposase enzyme having a second tagmentation profile; (c) combining a target nucleic acid with the first transposome and the second transposome under conditions suitable for tagmentation, thereby generating a tagmented nucleic acid.

In one aspect, disclosed herein are methods of sequential tagmentation. The methods include providing a first transposome. The first transposome comprises a first transposase enzyme having a first tagmentation profile. A target nucleic acid is combined with the first transposase enzyme under conditions suitable for tagmentation, thereby generating a tagmented nucleic acid. The tagmented nucleic acid is combined with a second transposome under conditions suitable for tagmentation. The second transposome comprises a second transposase enzyme having a second tagmentation profile.

Embodiment 1

A method of sequential tagmentation comprising: (a) providing a first transposome, the first transposome comprising a first transposon and a first transposase enzyme having a first tagmentation profile; (b) combining a target nucleic acid with the first transposase enzyme under conditions suitable for tagmentation, thereby generating a first tagmented nucleic acid; (c) combining the first tagmented nucleic acid with a second transposome under conditions suitable for tagmentation, the transposome comprising a second transposon and a second transposase enzyme having a second tagmentation profile, thereby generating a second tagmented nucleic acid.

Embodiment 2

The method of embodiment 1, wherein the first tagmentation profile and the second tagmentation profile are different.

Embodiment 3

The method of embodiment 1, comprising a wash step between steps (b) and (c) to substantially separate the tagmented nucleic from reaction buffer used in step (b).

Embodiment 4

The method of embodiment 3, wherein the wash step comprises binding the tagmented nucleic acid to a solid support.

Embodiment 5

The method of embodiment 4, wherein the solid support comprises beads.

Embodiment 6

The method of embodiment 4, wherein the solid support comprises a spin column.

Embodiment 7

The method of embodiment 1, wherein the first transposase and the second transposase have different insertion bias.

Embodiment 8

The method of embodiment 1, wherein step (c) comprises adding the second transposome to a reaction mixture comprising the first transposome.

Embodiment 9

The method of embodiment 1, wherein reaction buffer used in step (b) is diluted to permit tagmentation reaction with the second transposome.

Embodiment 10

A method of preparing a sequencing library, comprising: (a) providing a first transposome, the first transposome comprising a first transposon and a first transposase enzyme having a first tagmentation profile, wherein the first transposome is immobilized on a first solid support; (b) combining a target nucleic acid with the first transposase enzyme under conditions suitable for tagmentation, thereby generating a first tagmented nucleic acid; (c) combining the first tagmented nucleic acid with a second transposome under conditions suitable for tagmentation, the transposome comprising a second transposon and a second transposase enzyme having a second tagmentation profile, thereby generating a second tagmented nucleic acid and creating a sequencing library.

Embodiment 11

The method of embodiment 10, wherein the second transposome is immobilized on a second solid support.

Embodiment 12

The method of embodiment 11, wherein the first support and the second support are different.

Embodiment 13

A method of preparing a sequencing library, comprising: (a) providing a first transposome, the first transposome comprising a first transposon and a first transposase enzyme having a first tagmentation profile; (b) combining a target nucleic acid with the first transposase enzyme under conditions suitable for tagmentation, thereby generating a first tagmented nucleic acid; (c) combining the first tagmented nucleic acid with a second transposome under conditions suitable for tagmentation, the transposome comprising a second transposon and a second transposase enzyme having a second tagmentation profile, wherein the second transposome is immobilized on a second solid support, generating a second tagmented nucleic acid and creating a sequencing library.

Embodiment 14

The method of any one of embodiments 10-13, wherein the first and the second solid supports are beads.

Embodiment 15

The method of any one of embodiments 1-14, wherein the first transposon of the first transposome comprises a first adaptor and the second transposon of the second transposome comprises a second adaptor.

Embodiment 16

The method of embodiment 15, wherein the first and second adaptors comprise a sequence selected from the group consisting of barcodes, primer binding sequences, restriction endonuclease sites, and unique molecular indices.

Embodiment 17

The method of embodiment 9, wherein the first, second or both transposomes are immobilized on solid supports.

Embodiment 18

The method of embodiment 17, wherein the solid support is bead.

Embodiment 19

A method of preparing a sequencing library, comprising: (a) providing a first transposome, the first transposome comprising a first transposon and a first transposase enzyme having a first tagmentation profile; (b) combining a target nucleic acid with the first transposase enzyme under conditions suitable for tagmentation, thereby generating a first tagmented nucleic acid; (c) combining the first tagmented nucleic acid with a second transposome under conditions suitable for tagmentation, the transposome comprising a second transposon and a second transposase enzyme having a second tagmentation profile, thereby generating a second tagmented nucleic acid; (d) amplifying the second tagmented nucleic acid, thereby creating a sequencing library.

Embodiment 20

The method of any one of embodiments 1-19, further comprising amplifying the first tagmented nucleic acid.

Embodiment 21

The method of any one of embodiments 1-18, further comprising amplifying the second tagmented nucleic acid.

Embodiment 22

The method of embodiment 1-18, further comprising amplifying the first tagmented and second tagmented nucleic acid.

Embodiment 23

The method of embodiment 19, wherein the first, second or both transposomes are immobilized on solid supports.

Embodiment 24

The method of embodiment 23, wherein the solid support is bead.

Embodiment 25

A method of preparing a sequencing library, comprising: (a) providing a first transposome, the first transposome comprising a first transposon and a first transposase enzyme having a first tagmentation profile; (b) combining a target nucleic acid with the first transposase enzyme under conditions suitable for tagmentation, thereby generating a first tagmented nucleic acid; (c) substantially separating the first tagmented nucleic from reaction buffer used in step (b); (d) combining the first tagmented nucleic acid with a second transposome under conditions suitable for tagmentation, the second transposome comprising a second transposon and a second transposase enzyme having a second tagmentation profile, thereby generating a second tagmented nucleic acid; (e) amplifying the second tagmented nucleic acid, thereby generating a sequencing library.

Embodiment 26

The method of embodiment 25, further comprising optionally amplifying the first tagmented nucleic acid.

Embodiment 27

The method of any one of embodiments 25-26, wherein the first, second or both transposomes are immobilized on solid supports.

Embodiment 28

The method of embodiment 27, wherein the solid support is bead.

Embodiment 29

The method of any one of embodiments 19-28, wherein the first transposon comprises a first adaptor.

Embodiment 30

The method of any one of embodiments 19-28, wherein the second transposon comprises a second adaptor.

Embodiment 31

The method of any one of embodiments 19-28, wherein the first transposon comprises a first adaptor and the second transposon comprises a second adaptor, wherein the first and the second adaptors are different.

Embodiment 32

The method of any one of embodiments 19-31, wherein the first and second adaptors comprise a sequence selected from the group consisting of: barcodes, primer binding sequences, restriction endonuclease sites, and unique molecular indices.

Embodiment 33

The method of any one of embodiments 1-32, wherein the first transposase enzyme is selected from the group consisting of Mos-1, HyperMu™, Tn5, Ts-Tn5, Ts-Tn5059, Hermes, Tn7.

Embodiment 34

The method of any one of embodiments 1-32, wherein the second transposase enzyme is selected from the group consisting of Mos-1, HyperMu™, Tn5, Ts-Tn5, Ts-Tn5059, Hermes, Tn7.

Embodiment 35

The method of any of embodiments 1-34, wherein the methods are used for meta-genomics for microbial samples.

Embodiment 36

The method of any one of embodiments 1-35, wherein the first tagmentation profile and the second tagmentation profile are different, and wherein the two profiles have different percent of GC dropout.

Embodiment 37

The method of any one of embodiments 1-35, wherein the first tagmentation profile and the second tagmentation profile are different, and wherein the two profiles have different percent of AT dropout.

Embodiment 38

The method of anyone of embodiments 10-37, wherein reaction buffer used in step (b) is diluted to permit tagmentation reaction with the second transposome.

Embodiment 39

The method of anyone of embodiments 10-37, wherein the second transposome is combined to a reaction mixture comprising the first transposome and the first tagmented nucleic acid.

Embodiment 40

The method of embodiment 39, wherein one or more first transposase remains bound to the first tagmented nucleic acid during combining the first tagmented nucleic acid with a second transposome.

Embodiment 41

The method of embodiment 8, wherein one or more first transposase remains bound to the first tagmented nucleic acid during combining the first tagmented nucleic acid with a second transposome.

Embodiment 42

A method of tagmentation comprising: (a) providing a first transposome, the first transposome comprising a first transposon and a first transposase enzyme having a first tagmentation profile; (b) providing a second transposome, the second transposome comprising a second transposon and a second transposase enzyme having a second tagmentation profile; (c) combining a target nucleic acid with the first transposome and the second transposome under conditions suitable for tagmentation, thereby generating a tagmented nucleic acid.

Embodiment 43

The method of embodiment 42, wherein the first, second or both transposomes are immobilized on solid supports.

Embodiment 44

The method of embodiment 43, wherein the solid support is bead.

Embodiment 45

The method of any one of embodiments 42-44, wherein the first transposon comprises a first adaptor.

Embodiment 46

The method of any one of embodiments 42-44, wherein the second transposon comprises a second adaptor.

Embodiment 47

The method of any one of embodiments 42-44, wherein the first transposon comprises a first adaptor and the second transposon comprises a second adaptor, wherein the first and the second adaptors are different.

Embodiment 48

The method of any one of embodiments 42-47, wherein the first and second adaptors comprise a sequence selected from the group consisting of barcodes, primer binding sequences, restriction endonuclease sites, and unique molecular indices.

Embodiment 49

The method of any one of embodiments 42-48, wherein the first transposase enzyme is selected from the group consisting of Mos-1, HyperMu™, Tn5, Ts-Tn5, Ts-Tn5059, Hermes, Tn7.

Embodiment 50

The method of any one of embodiments 42-48, wherein the second transposase enzyme is selected from the group consisting of Mos-1, HyperMu™, Tn5, Ts-Tn5, Ts-Tn5059, Hermes, Tn7.

Embodiment 51

The method of any of embodiments 42-50, wherein the methods are used for meta-genomics for microbial samples.

Embodiment 52

The method of any one of embodiments 42-51, wherein the first tagmentation profile and the second tagmentation profile are different, and wherein the two profiles have different percent of GC dropout.

Embodiment 53

The method of any one of embodiments 42-51, wherein the first tagmentation profile and the second tagmentation profile are different, and wherein the two profiles have different percent of AT dropout.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 16 shows the sequences of HyperMu™ transposon and various primers used including MM1141 (SEQ ID NO:01), MM1138 (SEQ ID NO:02), MuPCRts (SEQ ID NO:03), P7MUTS (SEQ ID NO:04), and P5MUTS (SEQ ID NO:05).

FIG. 19 shows the statistics of a sequencing run of *E. Coli* chromosome using HyperMu™ tagmentation.

FIG. 22 A-D show the sequence bias of TruSeq, HyperMu™ and Tn5 (Nextera) and compared to a reference tagmentation. The DNA used in reference studies is *E. coli* DNA. % of GC is shown in x-axis and the frequency is shown in y-axis.

DETAILED DESCRIPTION

Figure 1:
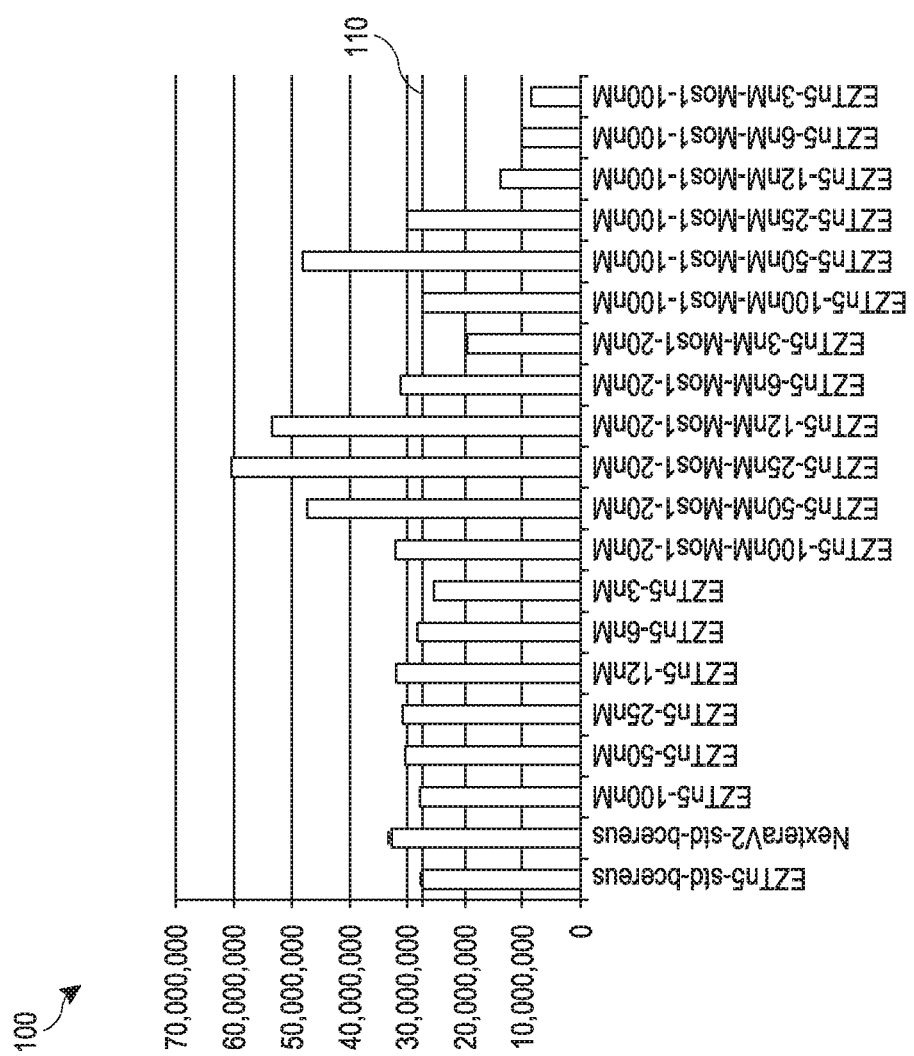
FIG. 1 shows a bar graph of the number of unique molecules in EZ-Tn5™ and EZ-Tn5™+Mos1 tagmented DNA libraries prepared using different concentrations of transposomes.

The transposase compositions and tagmentation methods provided herein have surprisingly improved properties including, for example, generating tagged DNA fragments that are qualitatively and quantitatively representative of the target nucleic acids in the sample from which they are generated.

Inventors of the present application have surprisingly and unexpectedly found that using two or more transposomes having two or more different tagmentation profiles provides a more uniform tagmentation of a target DNA. The inventors have also found that the use of two or more transposomes is specially advantageous when the tagmentation profiles of the transposases have different insertion biases such as different AT and GC dropout rates.

The methods and compositions provided herein are useful with transposase enzymes and methods as described in greater detail in the disclosure of U.S. 62/062,006, filed on Oct. 9, 2014 and entitled "MODIFIED TRANSPOSASES FOR REDUCTION OF INSERTION BIAS," the content of which is incorporated by reference herein in its entirety.

The methods and compositions provided herein are also useful with transposase enzymes and methods as described in greater detail in the disclosures of U.S. 2010/0120098 and 2014/0194324, the content of which is incorporated by reference herein in its entirety.

In one aspect, the methods disclosed herein include sequential tagmentation comprising: (a) providing a first transposome, the first transposome comprising a first transposon and a first transposase enzyme having a first tagmentation profile; (b) combining a target nucleic acid with the first transposase enzyme under conditions suitable for tagmentation, thereby generating a first tagmented nucleic acid; (c) combining the first tagmented nucleic acid with a second transposome under conditions suitable for tagmentation, the transposome comprising a second transposon and a second transposase enzyme having a second tagmentation profile, thereby generating a second tagmented nucleic acid.

In some embodiments, the method comprises a wash step between steps (b) and (c) to substantially separate the tagmented nucleic from reaction buffer used in step (b). In some embodiments, the wash step comprises binding the tagmented nucleic acid to a solid support. In some embodiments, the solid support comprises beads. In some embodiments, the solid support comprises a spin column. In some embodiments, step (c) comprises adding the second transposome to a reaction mixture comprising the first transposome. In some embodiments, one or more first transposases remained bound to the first tagmented nucleic acid during the combination of second transposome to the first tagmented nucleic acid.

In one aspect, disclosed herein are methods of preparing a sequencing library. The methods include providing a first transposome, the first transposome comprising a first transposon and a first transposase enzyme having a first tagmentation profile, in which the first transposome is immobilized on a first solid support. A target nucleic acid is combined with the first transposase enzyme under conditions suitable for tagmentation, thereby generating a first tagmented nucleic acid. The tagmented nucleic acid is combined with a second transposome under conditions suitable for tagmentation, the second transposome comprising a second transposon and a second transposase enzyme having a second tagmentation profile, thereby generating a second tagmented nucleic acid and creating a sequencing library.

In one aspect, disclosed herein are methods of preparing a sequencing library. The methods include providing a first transposome, the first transposome comprising a first transposon and a first transposase enzyme having a first tagmentation profile. A target nucleic acid is combined with the first transposase enzyme under conditions suitable for tagmentation, thereby generating a first tagmented nucleic acid. The first tagmented nucleic acid is combined with a second transposome under conditions suitable for tagmentation, the second transposome comprising a second transposon and a second transposase enzyme having a second tagmentation profile, in which the second transposome is immobilized on a second solid support, thereby generating a second tagmented nucleic acid and creating a sequencing library.

In one aspect, disclosed herein are methods of preparing a sequencing library. The methods include providing a first transposome, the first transposome comprising a first transposon and a first transposase enzyme having a first tagmentation profile. A target nucleic acid is combined with the first transposase enzyme under conditions suitable for tagmentation, thereby generating a first tagmented nucleic acid. The first tagmented nucleic acid is combined with a second transposome under conditions suitable for tagmentation, the transposome comprising a second transposon and a second transposase enzyme having a second tagmentation profile, thereby creating a sequencing library.

In one aspect, disclosed herein are methods of preparing a sequencing library. The methods include providing a first transposome, the first transposome comprising a first transposon and a first transposase enzyme having a first tagmentation profile. A target nucleic acid is combined with the first transposase enzyme under conditions suitable for tagmentation, thereby generating a first tagmented nucleic acid. The first tagmented nucleic acid is substantially separated from the reaction buffer used for the first tagmentation reaction. The first tagmented nucleic acid is then combined with a second transposome under conditions suitable for tagmentation, the second transposome comprising a second transposons and a second transposase enzyme having a second tagmentation profile, thereby generating a second tagmented nucleic acid. The second tagmented nucleic acid is amplified, thereby generating a sequencing library. In some embodiments, the first set of tagmented nucleic acid is optionally amplified.

In another aspect, the methods disclosed herein include tagmentation comprising: (a) providing a first transposome, the first transposome comprising a first transposon and a first transposase enzyme having a first tagmentation profile; (b) providing a second transposome, the second transposome comprising a second transposon and a second transposase enzyme having a second tagmentation profile; (c) combining a target nucleic acid with the first transposome and the second transposome under conditions suitable for tagmentation, thereby generating a tagmented nucleic acid. In some embodiments, the first and second transposomes are added simultaneously.

In some embodiments, the first transposon of the first transposome comprises first adaptor and the second transposon of the second transposome comprises a second adaptor. In some embodiments, the first and the second adaptors are different. In some embodiments, the first and second adaptors comprise a sequence selected from the group consisting of barcodes, primer binding sequences, restriction endonuclease sites, and unique molecular indices.

In some embodiments, the first, second, or both transposomes are immobilized on a second solid support. Exemplary solid supports include, but are not limited to beads, flow cell surface, spin column, column matrix. In some embodiments, the first surface and the second supports are different. In some embodiments, the first and the second solid supports are beads. In some embodiments, the first trasposomes are immobilized on a solid support. In some embodiments, the first transposomes immobilized on a solid support remain bound to the tagmented target nucleic acid and the first tagmented nucleic acids are separated from the solution using the solid support (e.g., streptavidin beads, magnetic beads etc.).

In some embodiments of the above aspects, the first tagmented nucleic acid is amplified before contacting the second transposome. In some embodiments of the above aspects, the second tagmented nucleic acid is amplified. In some embodiments, two sets of amplification are carried out. In the first set of amplification, the first tagmented nucleic acid is amplified. In the second set of amplification, the second tagmented nucleic acid is further amplified.

In some embodiments, the first tagmentation profile and the second tagmentation profile are different. In some embodiments, the first transposase and the second transposase have different insertion bias. In some embodiments, the first tagmentation and second profiles have different AT dropout rates. In some embodiments, the first and second tagmentation profiles have different GC dropout rates. In some embodiments, the first tagmentation profile has higher GC dropout rate as compared to the second tagmentation profile. In some embodiments, the first transposase has a greater insertion bias towards AT rich region as compared to the second transposase. In some embodiments, the second tagmentation profile has higher AT dropout rate as compared to the first tagmentation profile. In some embodiments, the second transposase has a greater insertion bias towards GC rich region as compared to the first transposase.

In some embodiments, the first tagmentation profile has higher AT dropout rate as compared to the second tagmentation profile. In some embodiments, the first transposase has a greater insertion bias towards GC rich region as compared to the second transposase. In some embodiments, the second tagmentation profile has higher GC dropout rate as compared to the first tagmentation profile. In some embodiments, the second transposase has a greater insertion bias towards AT rich region as compared to the second transposase.

In some embodiments, the reaction buffer used for the first tagmentation reaction is diluted to permit tagmentation reaction with the second transposome. In some embodiments, the reaction buffer used for the first tagmentation reaction is diluted to at least 1.5-fold, 2-fold, 2.5-fold, 3-fold, 4-fold, 5-fold, 6-fold, 7-fold, 8-fold, 9-fold, 10-fold, 12.5-fold, 15-fold, 20-fold, 25-fold, 30-fold, 40-fold, 50-fold, 60-fold, 70-fold, 80-fold, 90-fold, 100-fold, 125-fold, 200-fold, 250-fold, 300-fold or more. In some embodiments, the first tagmented nucleic acid remains immobilized on a solid support during the dilution. In some embodiments, the first tagmented nucleic acid remains bound to one or more first transposases during the dilution. In some embodiments, the first tagmented nucleic acid remains bound to one or more first transposomes and the first transposomes are immobilized on a solid support, thereby immobilizing the first tagmented nucleic acid.

In some embodiments, the first and second transposomes have different tagmentation profile for a particular genome.

In some embodiments, the first transposase for the first tagmentation reaction is Mos-1 and the second transposase for the second tagmentation reaction is Tn5 transposase (e.g., EZTn5™, NexteraV2, or TS-Tn5059).

In one embodiment, the first transposase for the first tagmentation reaction is Tn5 transposase (e.g., EZTn5™, NexteraV2, or TS-Tn5059) and a second transposase for the second tagmentation reaction is Mos1 transposases to generate a tagmented DNA library. In one example, the second tagmentation reaction using Mos1 is performed immediately after the first tagmentation reaction using Tn5 (i.e., a clean-up step is not used to remove Tn5 from the DNA before the second tagmentation reaction).

In another embodiment, the methods of the invention use a first tagmentation reaction using Mos1 transposases followed by a sample clean-up step and a second tagmentation reaction using Tn5 transposases (e.g., EZTn5™, NexteraV2, or TS-Tn5059) to generate a tagmented DNA library. In one example, the sample clean-up step is a DNA clean-up step performed using the DNA Clean & Concentrator™ kit (Zymo Research). In this clean-up step, Mos1 is denatured and removed from the DNA. In another example, the sample clean-up step is performed using Agencourt AMPure beads (Beckman Coulter, Inc.). In this example, the clean-up step is a buffer exchange step wherein the Mos1 transposomes remain bound to the DNA.

Figure 23:
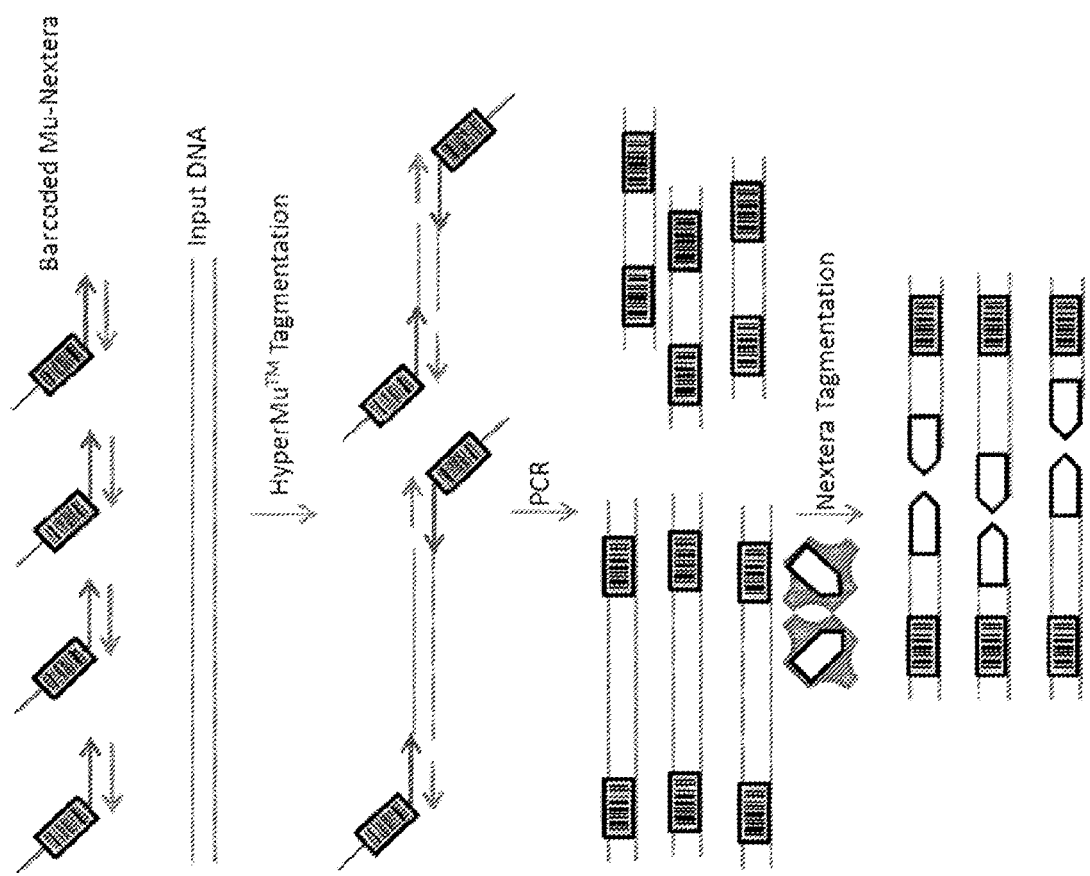
FIG. 23 shows an exemplary scheme of preparing sequence library by sequential tagmentation using HyperMu™ and Nextera transposomes.
Figure 24:
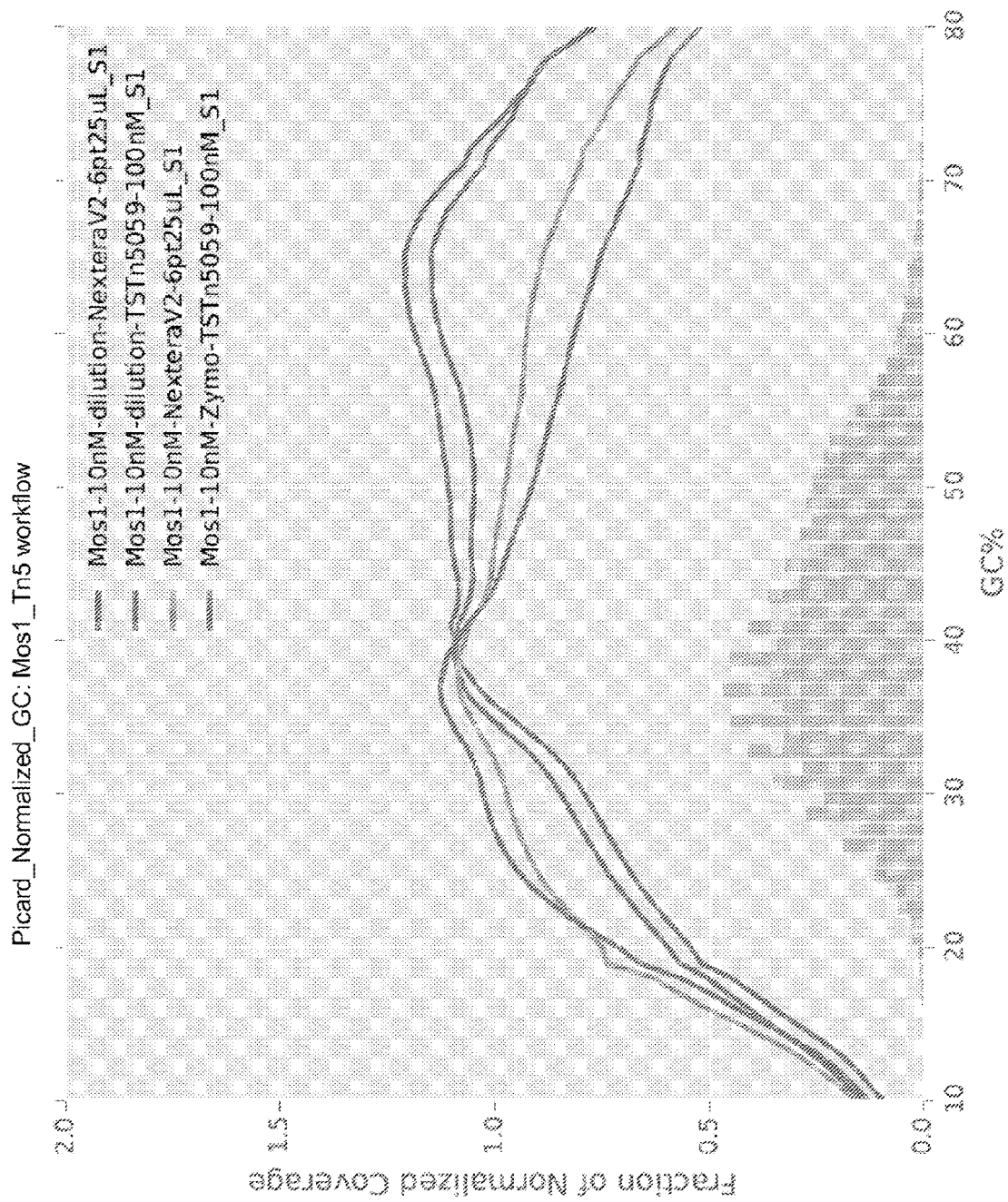
FIG. 24 shows a plot of fraction of normalized coverage as a function of % GC using Mos-1 tagmentation followed by TsTn5059/Nextera tagmentation. The experiments include two different workflows, one with a clean-up step between two tagmentation steps and the other where the buffer is adjusted by dilution between two tagmentation steps.
Figure 25:
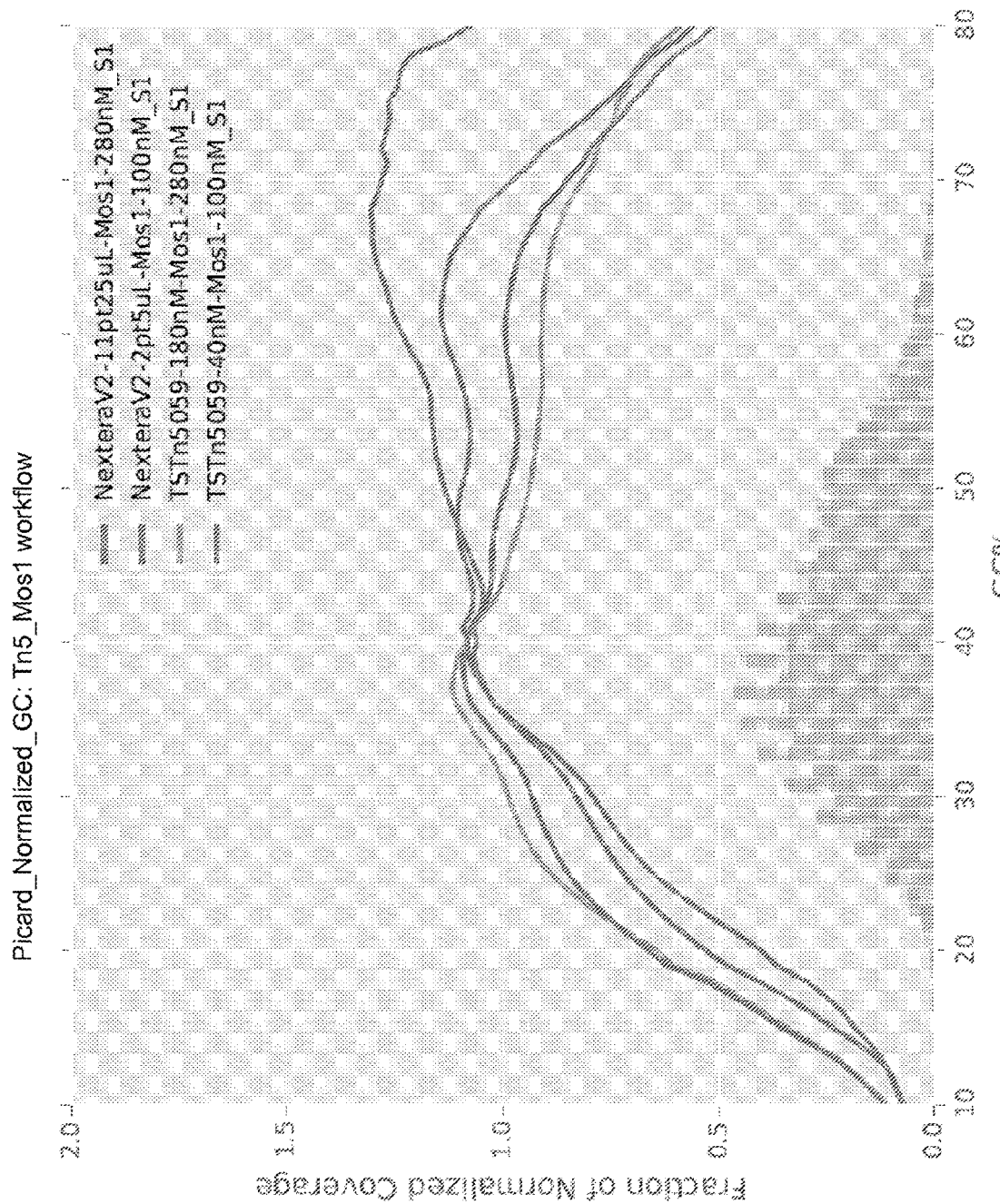
FIG. 25 shows a plot of fraction of normalized coverage as a function of % GC using TsTn5059/Nextera tagmentation followed by Mos-1 tagmentation.
Figure 26:
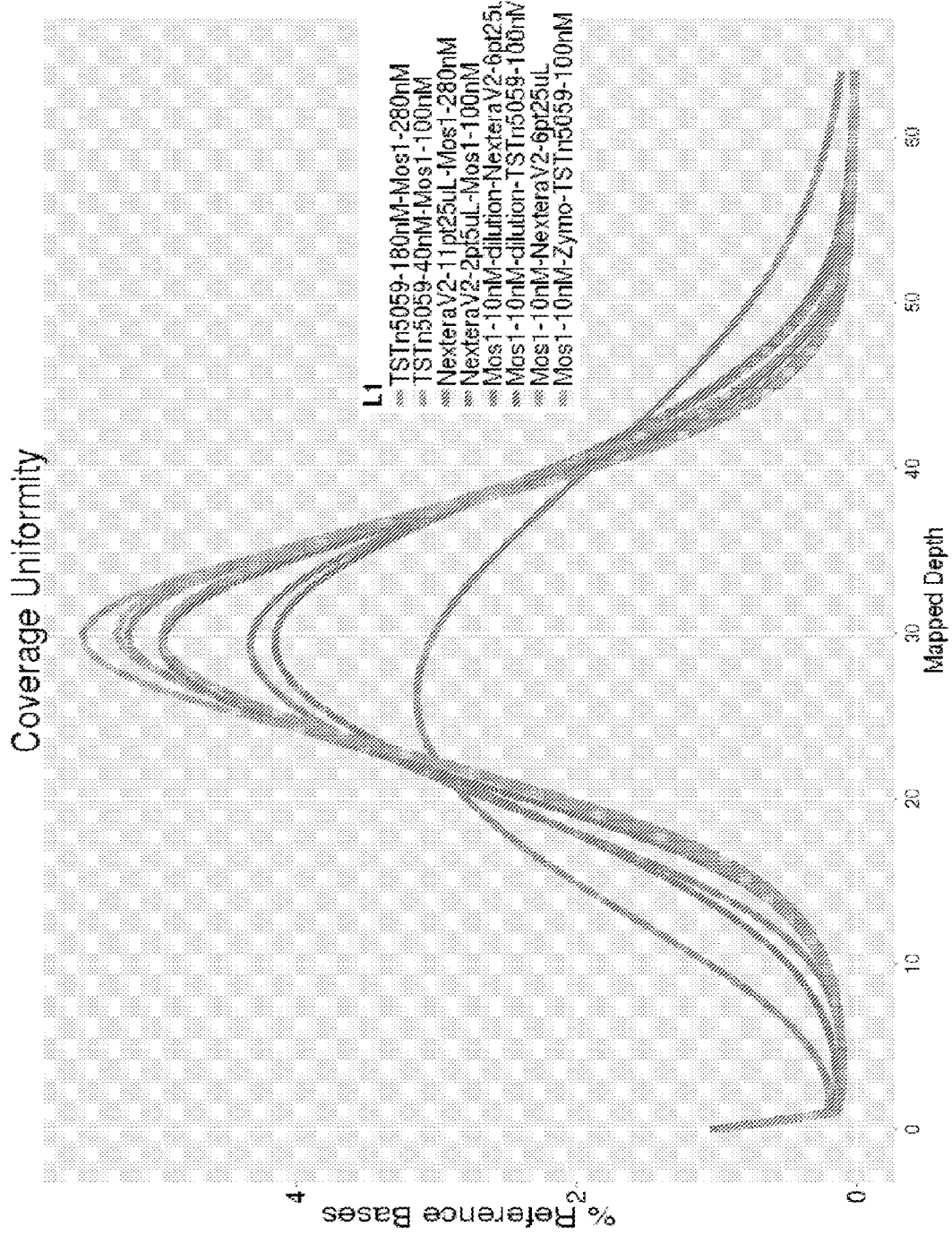
FIG. 26 shows a plot of coverage uniformity using various combination of Mos-1 and TsTn5059/Nextera enzymes at various concentrations.
Figure 27:
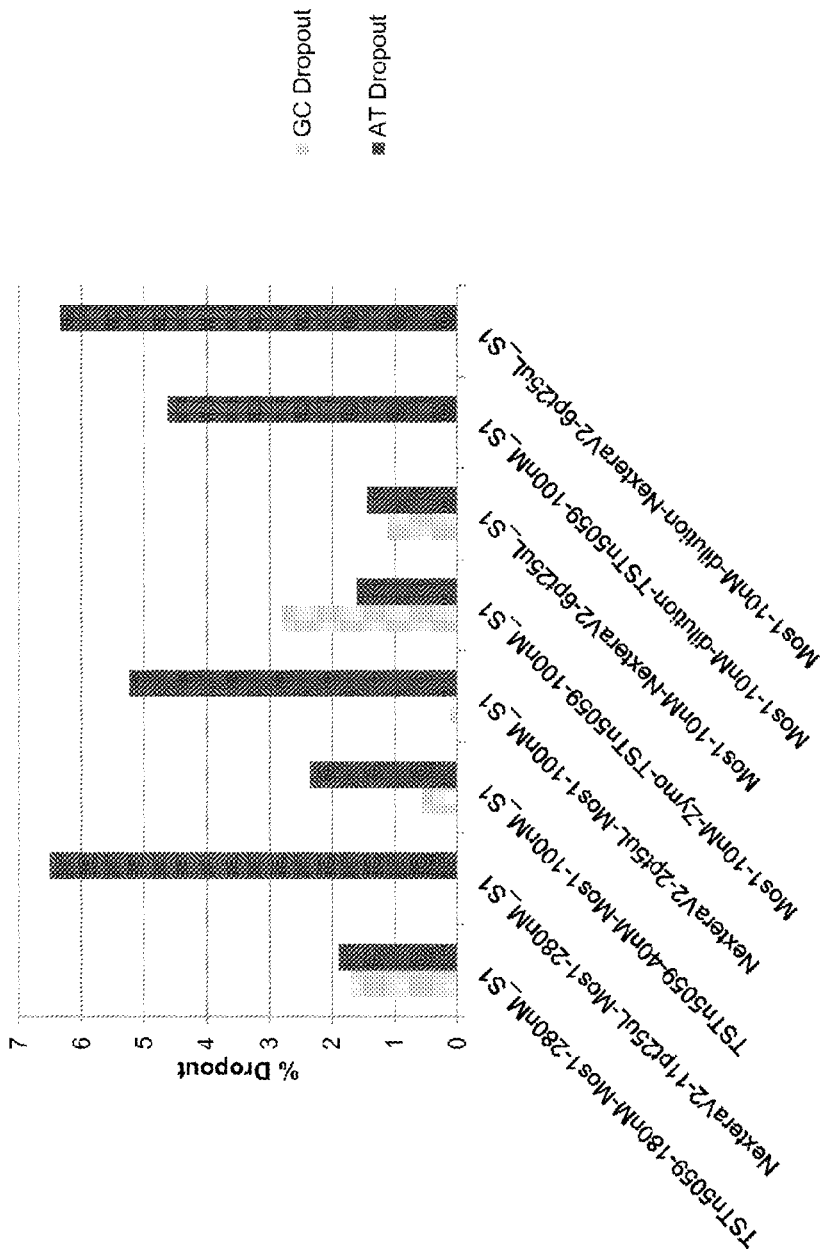
FIG. 27 shows a bar graph of the percent AT dropout and the percent GC dropout in the tagmented libraries using various combinations of TsTn5059/Nextera and Mos-1.
Figure 28:
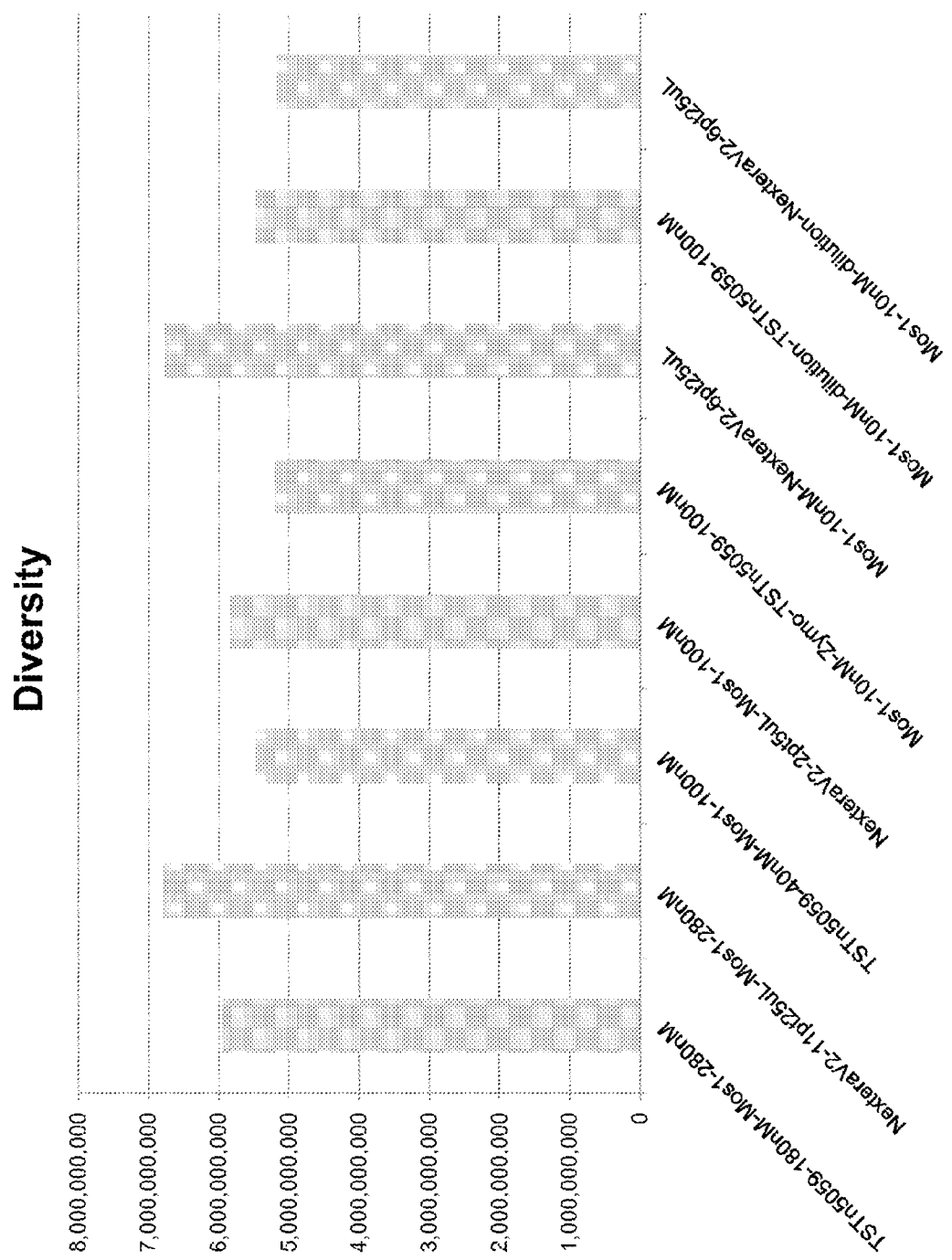
FIG. 28 shows a bar graph showing the diversity in TS-Tn5059/Nextera+Mos1 tagmented libraries prepared using different concentrations of transposomes.

In another embodiment, the methods of the invention use a first tagmentation reaction using Mu or HyperMu™ transposases transpososases followed by a sample clean-up step and a second tagmentation reaction using Tn5 transposases (e.g., EZTn5™, NexteraV2, or TS-Tn5059) to generate a tagmented DNA library. In one example, the sample clean-up step is a DNA clean-up step performed using the DNA Clean & Concentrator™ kit (Zymo Research). In this clean-up step, Mu or HyperMu™ is denatured and removed from the DNA. In another example, the sample clean-up step is performed using Agencourt AMPure beads (Beckman Coulter, Inc.). In this example, the clean-up step is a buffer exchange step wherein the Mu or HyperMu™ transposases remain bound to the DNA. FIG. 23 shows an exemplary scheme of preparing sequence library by sequential tagmentation using HyperMu™ and Nextera transposomes. The input DNA is first subjected to tagmentation using the individually tagged "Mu-Nextera" complex. This library is then amplified via PCR, so that every fragment is represented multiple times in the amplified reaction. The amplified library is taken through a 2nd round of tagmentation with the basic Nextera kit in a concentration regime in which the enzyme is the limiting factor. This guarantees that every single molecule is minimally tagmented with the Nextera complex to preserve maximum continuity information. The generated library is then sequenced. All the Nextera-fragments that have been generated from the same amplicon do share the same barcode (or end-tag), which can be used in the final assembly.

In some embodiments, the amount of first and the second transposases can be same. In some embodiments, the amount of first and the second transposases can be different.

In one embodiment, the methods are used for meta-genomics using microbial samples.

Sequential Tagmentation to Meta-Genomics and Microbiome

Sequential tagmentation in all its forms can be applied to microbial samples for meta-genomics applications. In some examples, the performance of a single transposase is highly affected by its bias and the sequence context of the target DNA. If the sample contains multiple species with different DNA sequence compositions, the tagmentation may perform better for some than the other. Genomic DNA for some species may end up with relatively larger or much smaller fragments, which skews their representation on the flowcell. This will cause missing of meta-genomics information. In extreme cases, some species may not have any representation on the flowcell.

Using sequential tagmentation can help lowering the overall tagmentation bias. In particular, different ratios of the two enzymes can be applied to tweak the library preparation for various genomic compositions. Multiple sequential tagmentations with different enzyme ratios can be applied to the same sample. This helps capturing wider range of species in a microbiome sample. For example, the sample can be split into multiple smaller samples and apply sequential tagmentations with different enzyme ratios on each. Different ratios of enzymes can help better capturing sequencing data of different species in the microbiome sample.

Furthermore, a quick screen can be established based on fragment size distribution. A microbiome sample (from a certain source, such as gut) can be split into smaller size samples, multiple sequential tagmentations with different enzyme ratios can be applied to each and fragment size distribution for each one can be stored as the baseline. Sample from the same source can be put through the same process and major changes in the fragment size distributions can point towards a major change in the microbiome. This can be used for a quick test to see whether a microbiome flora from a source is changing.

As used herein, the term "tagmentation" refers to the modification of DNA by a transposome complex comprising transposase enzyme and transposon end sequence in which the transposon end sequence further comprises adaptor sequence. Tagmentation results in the simultaneous fragmentation of the DNA and ligation of the adaptors to the 5' ends of both strands of duplex fragments.

Following a purification step to remove the transposase enzyme, additional sequences can be added to the ends of the adapted fragments, for example by PCR, ligation, or any other suitable methodology known to those of skill in the art.

The method of the invention can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

In standard sample preparation methods, each template contains an adaptor at either end of the insert and often a number of steps are required to both modify the DNA or RNA and to purify the desired products of the modification reactions. These steps are performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wis.).

More examples of transposition systems that can be used with certain embodiments provided herein include *Staphylococcus aureus* Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol. Methods 71:332-5). Additionally, the methods and compositions provided herein are useful with transposase of *Vibrio* species, including *Vibrio harveyi*, as set forth in greater detail in the disclosures of US 2014/0093916 and 2012/0301925, each of which is incorporated by reference in its entirety.

Briefly, a "transposition reaction" is a reaction wherein one or more transposons are inserted into target nucleic acids at random sites or almost random sites. Essential components in a transposition reaction are a transposase and DNA oligonucleotides that exhibit the nucleotide sequences of a transposon, including the transferred transposon sequence and its complement (i.e., the non-transferred transposon end sequence) as well as other components needed to form a functional transposition or transposome complex. The DNA oligonucleotides can further comprise additional sequences (e.g., adaptor or primer sequences) as needed or desired.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein the term "about" means+/−10%.

Solid Support

In some embodiments, the solid support or its surface is non-planar, such as the inner or outer surface of a tube or vessel. In some embodiments, the solid support is a surface of a flow cell. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads. In some embodiments, the beads can be color coded. For example, MicroPlex® Microspheres from Luminex, Austin, Tex. may be used.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 μm in diameter.

Barcodes

Generally, a barcode can include one or more nucleotide sequences that can be used to identify one or more particular nucleic acids. The barcode can be an artificial sequence, or can be a naturally occurring sequence generated during transposition, such as identical flanking genomic DNA sequences (g-codes) at the end of formerly juxtaposed DNA fragments. In some embodiments, a barcode is an artificial sequence that is non-natural to the target nucleic acid and is used to identify the target nucleic acid or determine the contiguity information of the target nucleic acid.

A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, such as transposomes comprising two non-contiguous transposon sequences, the first transposon sequence comprises a first barcode, and the second transposon sequence comprises a second barcode. In some embodiments, a transposon sequence comprises a barcode comprising a first barcode sequence and a second barcode sequence. In some of the foregoing embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different. The first and second barcode sequences may comprise a bi-code.

In some embodiments of compositions and methods described herein, barcodes are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomics sequencing, and in sample sequencing of a genome.

Exemplary barcode sequences include, but are not limited to TATAGCCT, ATAGAGGC, CCTATCCT, GGCTCTGA, AGGCGAAG, TAATCTTA, CAGGACGT, and GTACTGAC.

Target Nucleic Acids

A target nucleic acid can include any nucleic acid of interest. Target nucleic acids can include DNA, RNA, peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof. In a preferred embodiment, genomic DNA or amplified copies thereof are used as the target nucleic acid. In another preferred embodiment, cDNA, mitochondrial DNA or chloroplast DNA is used.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500 or 1000 nucleotides or more. Repeat sequences can be repeated, either contiguously or non-contiguously, any of a variety of times including, for example, 2, 3, 4, 5, 6, 7, 8, 9, 10, 15 or 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, organisms, single cell, or a single organelle. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium*, and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human). Target nucleic acids and template nucleic acids can be enriched for certain sequences of interest using various methods well known in the art. Examples of such methods are provided in Int. Pub. No. WO/2012/108864, which is incorporated herein by reference in its entirety. In some embodiments, nucleic acids may be further enriched during methods of preparing template libraries. For example, nucleic acids may be enriched for certain sequences, before insertion of transposomes after insertion of transposomes and/or after amplification of nucleic acids.

In addition, in some embodiments, target nucleic acids and/or template nucleic acids can be highly purified, for example, nucleic acids can be at least about 70%, 80%, 90%, 95%, 96%, 97%, 98%, 99%, or 100% free from contaminants before use with the methods provided herein. In some embodiments, it is beneficial to use methods known in the art that maintain the quality and size of the target nucleic acid, for example isolation and/or direct transposition of target DNA may be performed using agarose plugs. Transposition can also be performed directly in cells, with population of cells, lysates, and non-purified DNA.

In some embodiments, target nucleic acid can be from a single cell. In some embodiments, target nucleic acid can be from formalin fixed paraffin embedded (FFPE) tissue sample. In some embodiments, target nucleic acid can be cross-linked nucleic acid. In some embodiments, the target nucleic acid can be cross-linked to nucleic acid. In some embodiments, the target nucleic acid can be cross-linked to proteins. In some embodiments, the target nucleic acid can be cell-free nucleic acid. Exemplary cell-free nucleic acid include but are not limited to cell-free DNA, cell-free tumor DNA, cell-free RNA, and cell-free tumor RNA.

In some embodiments, target nucleic acid may be obtained from a biological sample or a patient sample. The term "biological sample" or "patient sample" as used herein includes samples such as tissues and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma and serum are examples of acellular bodily fluids. A sample may include a specimen of natural or synthetic origin (i.e., a cellular sample made to be acellular).

The term "Plasma" as used herein refers to acellular fluid found in blood. "Plasma" may be obtained from blood by removing whole cellular material from blood by methods known in the art (e.g., centrifugation, filtration, and the like).

Methods of Use

The transposases presented herein can be used in a sequencing procedure, such as an in vitro transposition technique. Briefly, in vitro transposition can be initiated by contacting a transposome complex and a target DNA. Exemplary transposition procedures and systems that can be readily adapted for use with the transposases of the present disclosure are described, for example, in WO 10/048605; US 2012/0301925; US 2013/0143774, each of which is incorporated herein by reference in its entirety.

For example, in some embodiments, the transposase enzymes presented herein can be used in a method for generating a library of tagged DNA fragments from target DNA comprising any dsDNA of interest (e.g., for use as next-generation sequencing or amplification templates), the method comprising: incubating the target DNA in an in vitro transposition reaction with at least one transposase and a transposon end composition with which the transposase forms a transposition complex, the transposon end composition comprising (i) a transferred strand that exhibits a transferred transposon end sequence and, optionally, an additional sequence 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end; and then joining the 3'-ends of the 5'-tagged DNA fragments to the first tag or to a second tag, thereby generating a library of tagged DNA fragments (e.g., comprising either tagged circular ssDNA fragments or 5'- and 3'-tagged DNA fragments (or "di-tagged DNA fragments")).

As used herein the term "diversity" refers to the number of unique molecules in a library. In some embodiments, diversity is an indication of the diversity (complexity) of the library.

As used herein "insert size" means average fragment size for the library. The mode and mean insert sizes were determined based on sequencing data, after determining the length of the sequenced insert. In some embodiments, fragment size is determined using a BioAnalyzer.

As used herein "GC dropout" means the percentage of GC rich regions in the genome that are dropped (absent) from the tagmented library.

As used herein "AT dropout" means the percentage of AT rich regions in the genome that are dropped (absent) from the tagmented library.

As used herein, the term "insertion bias" refers to the sequence preference of a transposase for insertion sites. For example, if the background frequency of A/T/C/G in a polynucleotide sample is equally distributed (25% A, 25% T, 25% C, 25% G), then any over-representation of one nucleotide over the other three at a transposase binding site or cleavage site reflects an insertion bias at that site. Insertion bias can be measured using any one of a number of methods known in the art. For example, the insertion sites can be sequenced and the relative abundance of any particular nucleotide at each position in an insertion site can be compared.

Unless otherwise specified, the terms "a" or "an" mean "one or more" throughout this application.

EXAMPLES

Example 1

Tn5 and Mos1 Sequential Tagmentation
Tn5 Tagmentation Followed by Mos1 Tagmentation In some experiments, first tagmentation reaction using Tn5 transposomes (e.g., EZTn5™, NexteraV2, or TS-Tn5059) and a second tagmentation reaction using Mos1 transposomes to generate a tagmented DNA library. In one example, the second tagmentation reaction using Mos1 is performed immediately after the first tagmentation reaction using Tn5 (i.e., a clean-up step is not used to remove Tn5 from the DNA before the second tagmentation reaction). The Tn5 enzyme used was either EZTn5, Tn5 from Nextera V2 kit, or mutant TS-Tn5059.

To evaluate the effect of sequential tagmentation using Tn5 and Mos1 transposomes on library output and sequencing metrics, tagmented DNA libraries were constructed using Bacillus cereus genomic DNA. For each sequentially tagmented library, a first tagmentation reaction was performed by mixing 20 μL B. cereus genomic DNA (50 ng), 25 μL 2× standard tagmentation buffer (2×TD; 20 mM Tris Acetate, pH 7.6, 10 mM MgCl2, and 20% dimethylformamide (DMF)), and various concentrations of EZ-Tn5™ transposomes (Epicentre) in a total reaction volume of 50 μL. EZ-Tn5™ transposome was used at final concentrations of 3, 6, 12, 25, 50, and 100 nM. Reactions were incubated at 55° C. for 5 minutes. After completion of the first tagmentation reaction, a second tagmentation reaction using Mos1 transposomes was performed. Mos1 transposome was used at final concentrations of 20 and 100 nM. Reactions using Mos1 also included the addition of NaCl at a final concentration of 200 mM. Reactions were incubated at 30° C. for 60 minutes.

For each Tn5 control library, a tagmentation reaction was performed by mixing 20 μL B. cereus genomic DNA, 25 μL 2× standard tagmentation buffer, and 5 μL of EZ-Tn5™ (25 nM) or NexteraV2 (25 nM) transposomes in a total reaction volume of 50 μL. Reactions were incubated at 55° C. for 5 minutes.

Following the tagmentation reaction, the samples were processed according to the rest of the standard Nextera™ sample preparation protocol (after tagmentation reaction) Libraries were sequenced by sequencing-by-synthesis (SBS) and evaluated by standard next generation sequencing analysis tools. Fragment size distribution in each library was also evaluated on a Bioanalyzer.

FIG. 1 shows a bar graph 100 of the number of unique molecules in EZ-Tn5™ and EZ-Tn5™+Mos1 tagmented DNA libraries prepared using different concentrations of transposomes. The number of unique molecules in a library is an indication of the diversity (complexity) of the library. Each bar on the graph represents a tagmented library. Control libraries (i.e., libraries that were prepared using standard reaction conditions of 25 nM EZ-Tn5™ or NexteraV2 transposomes) are designated by "std". Libraries that were prepared using different concentrations of EZ-Tn5™ are designated by "EZTn5-enzyme concentration". For example, the third bar in bar graph 100 is labeled "EZTn5-100 nM" and designates a library that was prepared using EZ-Tn5™ at a final concentration of 100 nM. Libraries that were prepared using sequential tagmentation with EZ-Tn5™ followed by Mos1 are designated by "EZTn5-enzyme concentration-Mos1-enzyme concentration". For example, the ninth bar in bar graph 100 is labeled "EZTN5-100 nM-Mos1-20 nM" and designates a library that was prepared using EZ-Tn5™ at a final concentration of 100 nM followed by tagmentation using Mos1 at a final concentration of 20 nM. All libraries were prepared using the standard buffer formulation. A line 110 indicates a standard level of diversity obtained in a Tn5 tagmented DNA library.

The data show that tagmented libraries prepared using EZ-Tn5™ at 12 nM-50 nM and Mos1 sequential tagmentation at 20 nM have a higher average diversity compared to control libraries and libraries prepared using EZ-Tn5™ alone. For example, the "EZTn5-25 nM-Mos1-20 nM" library has about a two-fold increase in diversity compared to control libraries or libraries prepared using EZ-Tn5™ alone.

Figure 2:
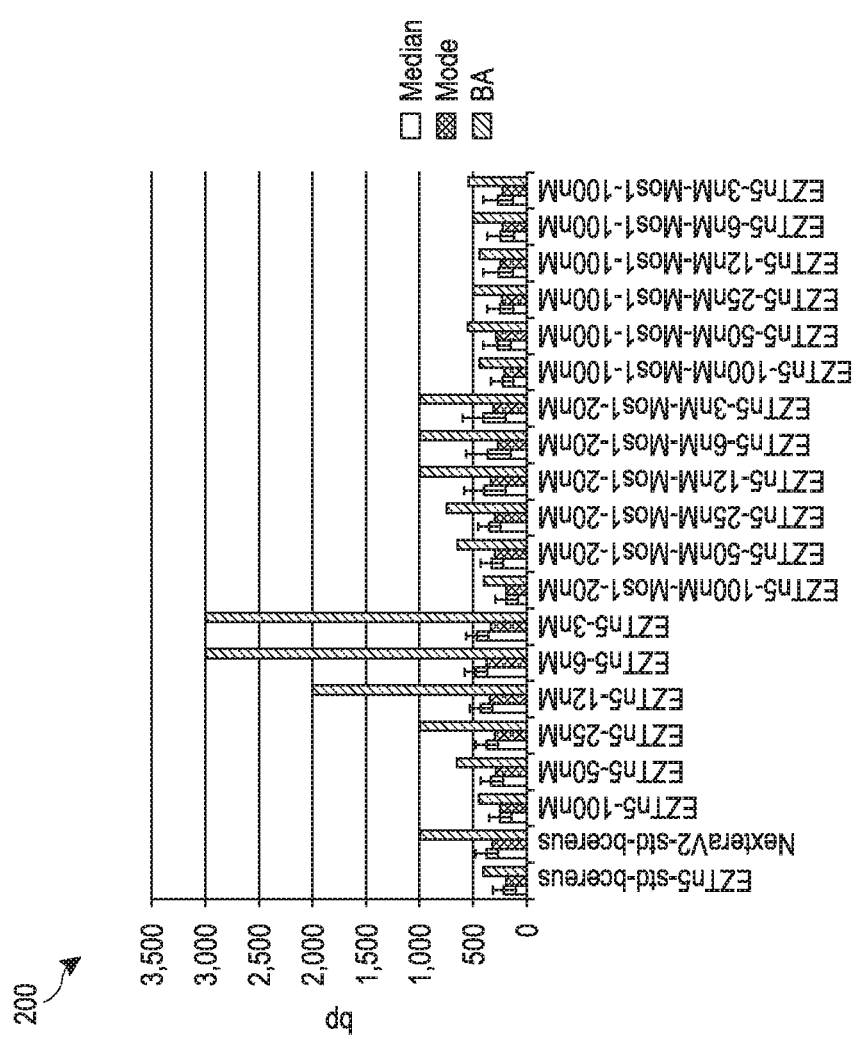
FIG. 2 shows a bar graph of the insert size in the tagmented libraries of FIG. 1.

FIG. 2 shows a bar graph 200 of the insert size in the tagmented libraries of FIG. 1. The median value and mode value for each tagmented library were generated from the SBS data. Because the median and mode values were generated from the SBS data, only those inserts that were amplified in the cluster amplification process and sequenced are represented. The "BA" value was generated from a Bioanalyzer trace of the fragment size distribution in each tagmented sample. Because the "BA" value was generated from the Bioanalyzer trace, all fragments generated in the tagmentation reaction are represented (i.e., larger fragments that may not be represented in the SBS data). The data show that there is variability in the insert size in libraries prepared using different concentrations of transposomes. The data also shows that in the "EZTn5-25 nM-Mos1-20 nM", which is the library with the highest level of diversity (FIG. 1), the insert size is about the same as the insert size in the "EZTn5-25 nM" library.

Figure 3:
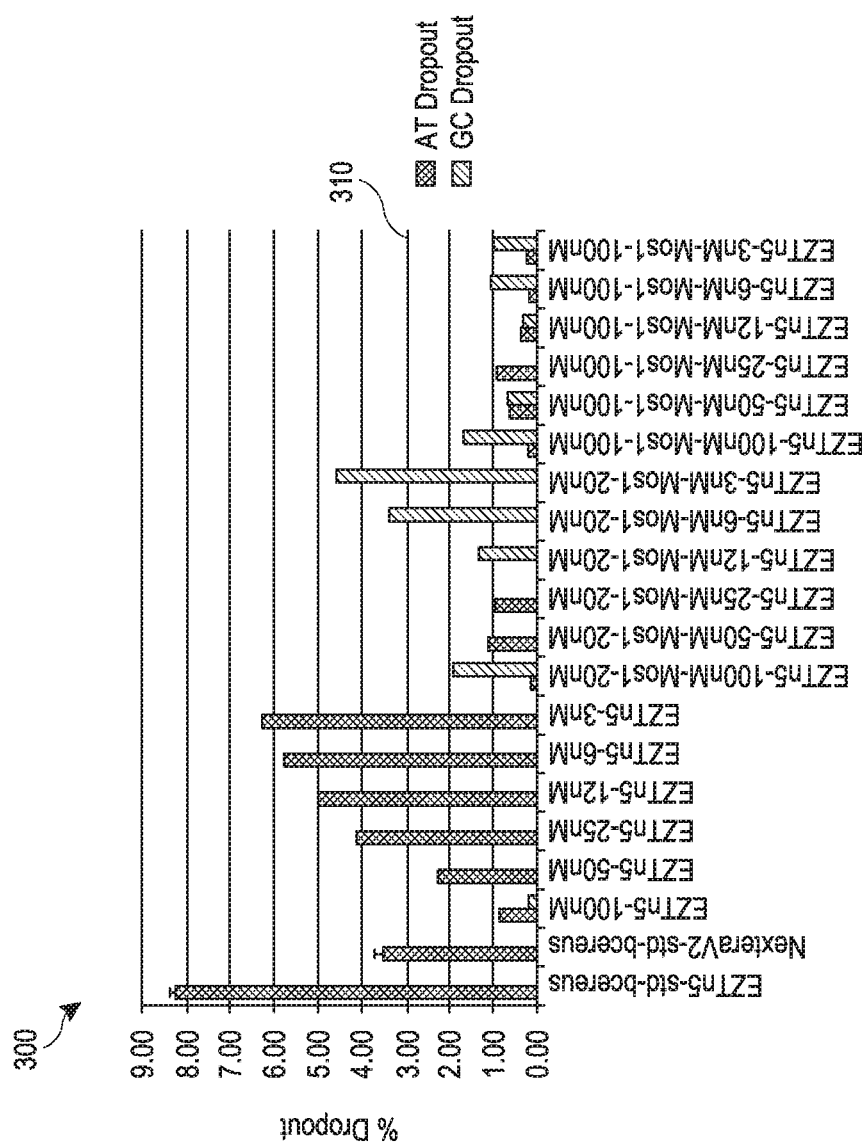
FIG. 3 shows a bar graph of the percent AT dropout and the percent GC dropout in the tagmented libraries of FIG. 1.

FIG. 3 shows a bar graph 300 of the percent AT dropout and the percent GC dropout in the tagmented libraries of FIG. 1. AT dropout may be defined as the percentage of AT rich regions in the genome that are not present in the tagmented library. GC dropout may be defined as the percentage of GC rich regions in the genome that are not present in the tagmented library. A line 310 indicates a standard threshold of AT dropout obtained in a standard Tn5 tagmentation reaction. In a standard Tn5 tagmentation reaction, GC dropout is not typically observed. The data show that there is variability in the percent AT and GC dropout prepared using different transposome concentrations. The data also shows that in the "EZTn5-25 nM-Mos1-20 nM", which is the library with the highest level of diversity (FIG. 1), the percent AT and GC dropout is substantially lower than the percent dropout in the control libraries, e.g., "EZTn5-std-bcereus", "NexteraV2-std-bcereus", and "EZTn5-25 nM".

To evaluate the effect of tagmentation buffer composition on library output and sequencing metrics, B. cereus tagmented libraries were prepared using modified formulations of the standard tagmentation buffer. The buffer formulations were as follows standard buffer (TD) (10 mM Tris Acetate, pH 7.6, 5 mM MgCl2, and 10% DMF); manganese buffer (Mn; 10 mM Tris Acetate, pH 7.6, 5 mM MnCl2, and 10% DMF); cobalt buffer (Co; 10 mM Tris Acetate, pH 7.6, 5 mM CoCl2, and 10% DMF); and nickel buffer (Ni; 10 mM Tris Acetate, pH 7.6, 5 mM NiCl2, and 10% DMF).

Figure 4:
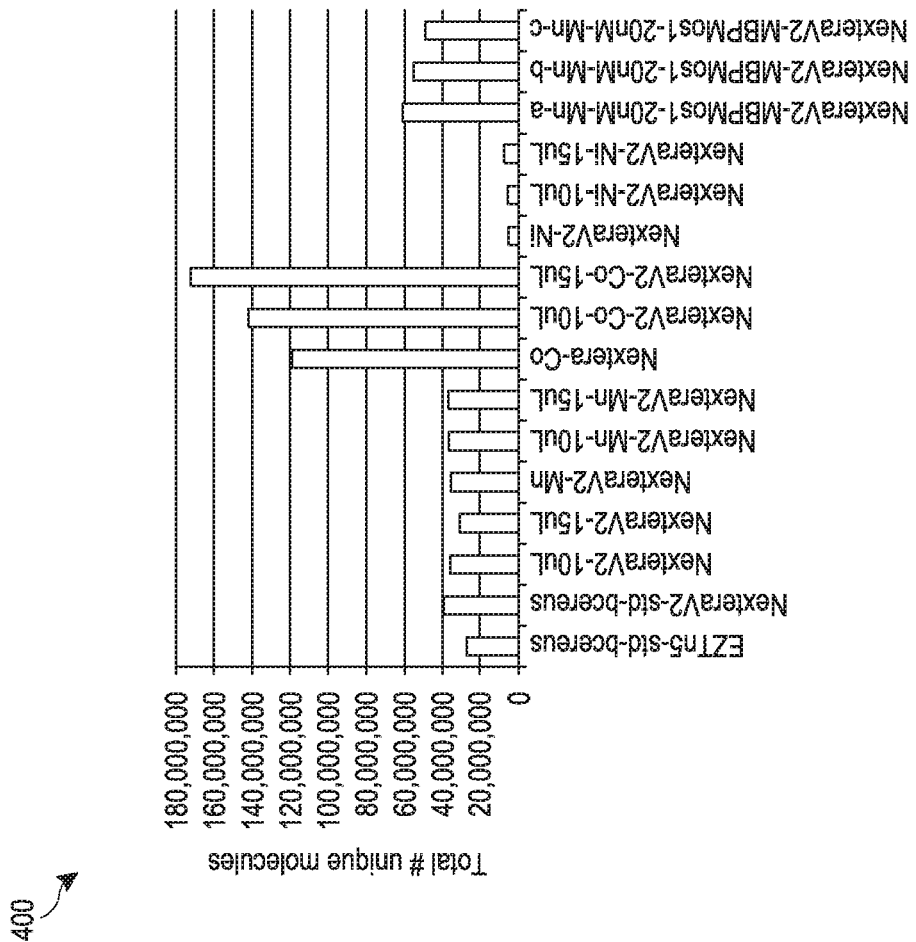
FIG. 4 shows a plot of the number of unique molecules in tagmented DNA libraries prepared using different tagmentation buffer formulations.

FIG. 4 shows a plot 400 of the number of unique molecules in tagmented DNA libraries prepared using different tagmentation buffer formulations. Control libraries that were prepared using the standard tagmentation buffer and volume of transposomes (5 µL=25 nM transposome) are designated "EZTn5-std-bcereus" and "NexteraV2-std-bcereus". Libraries that were prepared using different volumes (i.e., 10 µL or 15 µL; or 50 nM and 75 nM, respectively) of NexteraV2 transposome and the standard tagmentation buffer formulation are designated by "NexteraV2-10 µL" and "NexteraV2-15 µL". NexterV2 libraries that were prepared using a modified (e.g., Mn, Co, or Ni) tagmentation buffer formulation are designated by "NexteraV2-modification" or a "NexteraV2-modification-µL", where "µL" designates the volume of transposome used in the reaction. Libraries that were prepared using sequential tagmentation with NexteraV2 (25 nM) and Mos1 are designated by "NexteraV2-MBPMos1-20 nM-Mn", where 20 nM is the concentration of Mos1 transposome and "Mn" is the manganese buffer formulation. The sequential tagmentation library reaction was repeated three times (n=3) and the individual libraries are designated as a, b or c.

The data show that NexteraV2-tagmented libraries prepared using a tagmentation buffer that includes CoCl2 have a higher diversity compared to libraries prepared in buffers without the addition of CoCl2 (i.e., the standard tagmentation buffer and buffers that include MnCl2 or NiCl2). The data also shows that libraries prepared using sequential tagmentation with NexteraV2 and Mos1 in Mn buffer have a higher diversity compared to tagmented libraries prepared with NexteraV2 alone in Mn buffer.

Figure 5:
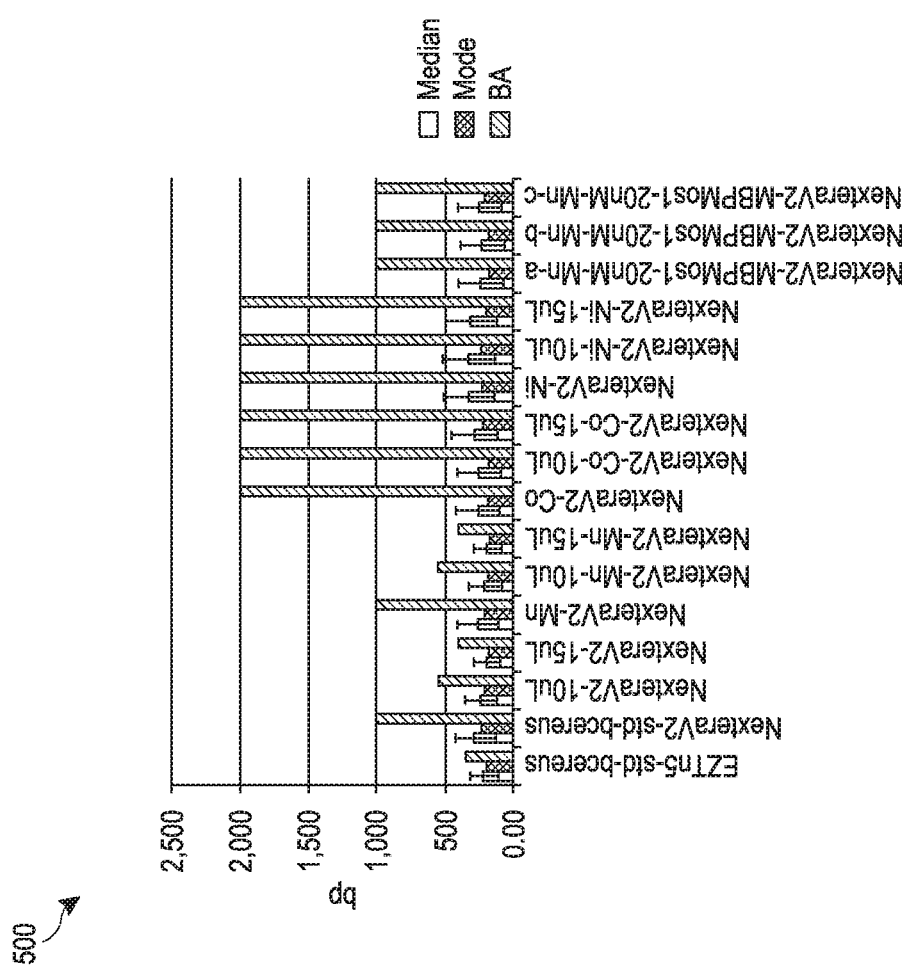
FIG. 5 shows a bar graph of the insert size in the tagmented libraries of FIG. 4.

FIG. 5 shows a bar graph 500 of the insert size in the tagmented libraries of FIG. 4. The data show that insert size in NexteraV2-tagmented libraries prepared using tagmentation buffers that include either CoCl2 or NiCl2 are relatively larger compared to tagmented libraries prepared using the standard or Mn buffer formulations. The data also show that in the "NexteraV2-MBPMos1-20 nM-Mn" sequentially tagmented libraries the insert size is about the same as the NextaraV2 control library ("NexteraV2-std-bcereus") and NexteraV2 library prepared in Mn buffer ("NexteraV2-Mn").

Referring now to FIG. 4 and FIG. 5, the data also shows that in sequentially-tagmented libraries prepared using the Mn buffer formulation (NexteraV2-MBPMos1-20 nM-Mn), library diversity is increased (relative to control levels) while the insert size in the library remains about the same (relative to control levels).

Figure 6:
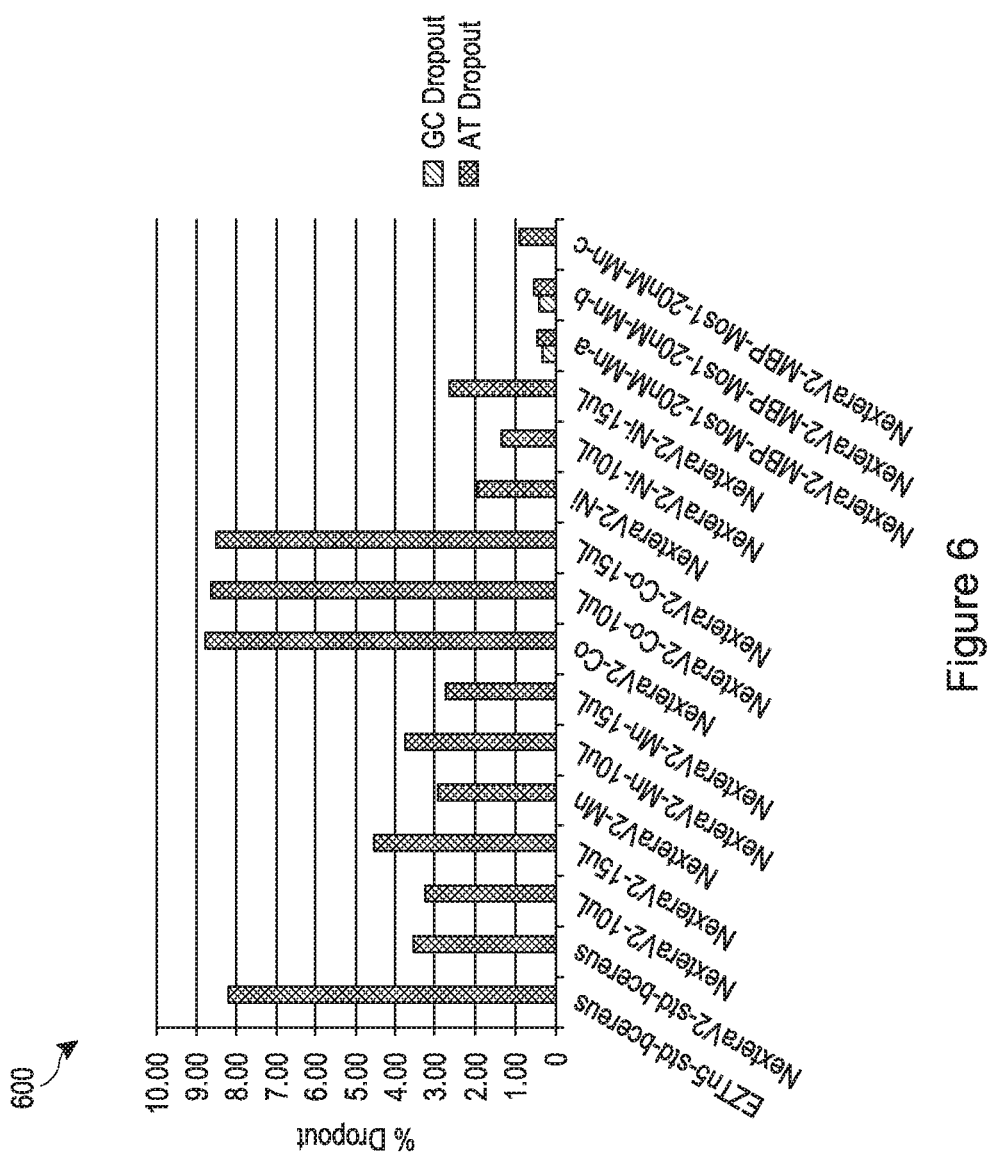
FIG. 6 shows a bar graph of the percent AT dropout and the percent GC dropout in the tagmented libraries of FIG. 4.

FIG. 6 shows a bar graph 600 of the percent AT dropout and the percent GC dropout in the tagmented libraries of FIG. 4. The data show that in the libraries prepared using Mn buffer and sequential tagmentation with NexterV2 and Mos1 (i.e., "EZTn5-25 nM-Mos1-20 nM") there is a substantial decrease in the percent AT dropout and a slight increase in the percent GC dropout compared to libraries prepared using NexteraV2 alone and either the standard tagmentation buffer (i.e., "NexteraV2-std-bcereus") or Mn buffer ("NexteraV2-Mn).

Referring now to FIGS. 4 through 6, the data shows that in the sequentially-tagmented libraries prepared using the Mn buffer formulation (NexteraV2-MBPMos1-20 nM-Mn), library diversity (FIG. 4) is increased while the insert size (FIG. 5) in the library remains about the same, and the percent AT dropout (FIG. 6) is substantially reduced.

In another example, the Tn5 transposome TS-Tn5059 and Mos1 were used to generate sequentially-tagmented B. cereus libraries. In this example, a first tagmentation reaction was performed using TS-TN5059 at final concentrations of 40 nM, 80 nM, and 240 nM. A second tagmentation reaction was performed using Mos1 at final concentrations of 10 and 20 nM. All libraries were prepared using the standard buffer formulation. Reactions using Mos1 also included the addition of NaCl at a final concentration of 200 mM. Following the tagmentation reaction, the samples were processed according to the standard Nextera™ sample preparation protocol. Libraries were evaluated by SBS on a MiSeq instrument (Illumina, Inc.). Fragment size distribution in each library was also evaluated on a Bioanalyzer.

Figure 7:
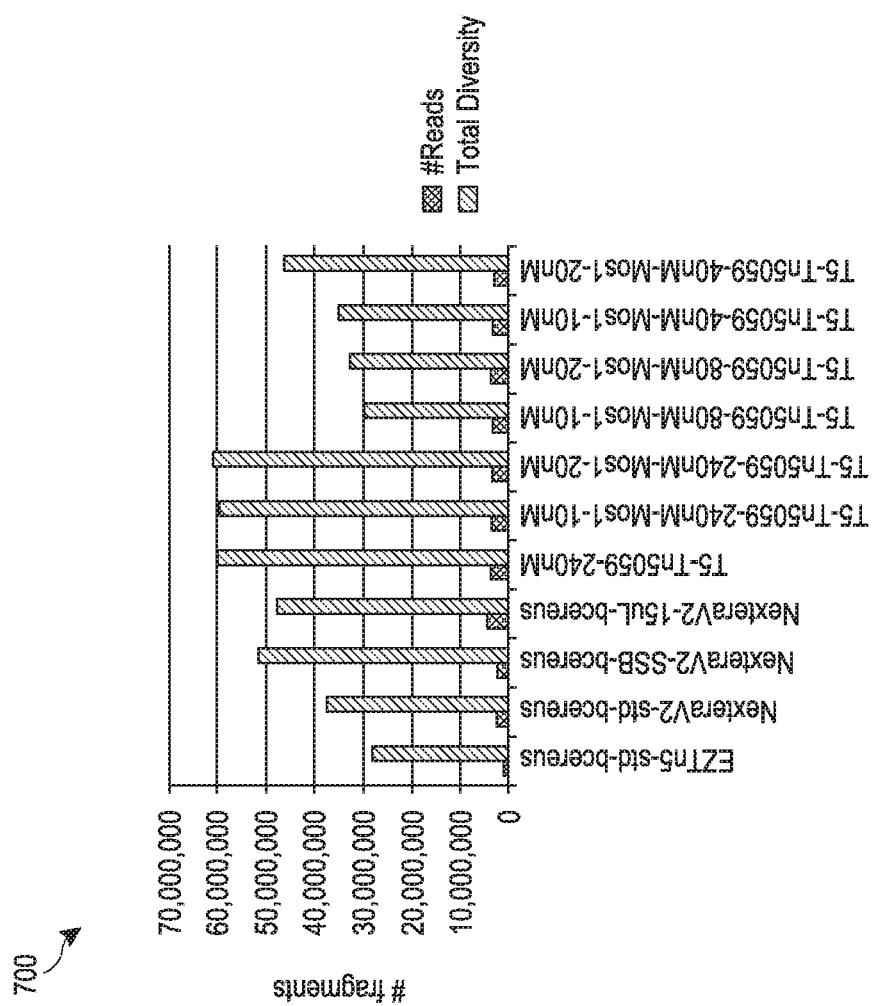
FIG. 7 shows a bar graph of the total number of reads and diversity in TS-Tn5059+Mos1 tagmented libraries prepared using different concentrations of transposomes.

FIG. 7 shows a bar graph 700 of the total number of reads and diversity in TS-Tn5059+Mos1 tagmented libraries prepared using different concentrations of transposomes. The total number of reads is the total number of reads from the flow cell. The diversity is the number of unique molecules in the library and is used as an indication of library complexity. Each pair of bars on the graph represents a tagmented library. Libraries that were prepared using sequential tagmentation with TS-Tn5059 and Mos1 are designated by "TS-Tn5059-enzyme concentration-Mos1-enzyme concentration". EZTn5™ and NexteraV2 were used to prepare comparative control libraries (e.g., "EZTn5-std-bcereus" and "NexteraV2-std-bcereus"). "NexteraV2-SSB-bcereus" designates a library that was prepared using the standard volume (5 µL) of transposome, but included an additional 10 µl of SSB diluent. "NexteraV2-15 µL-bcereus" designates a library that was prepared using 15 µL (75 nM) of NexterV2 transposome. All libraries were prepared using the standard buffer formulation.

The data shows that the diversity in the TS-Tn5059-240 nM-Mos1-20 nM library is higher compared to the diversity in the EZTn5™ and NexteraV2 control libraries.

Figure 8:
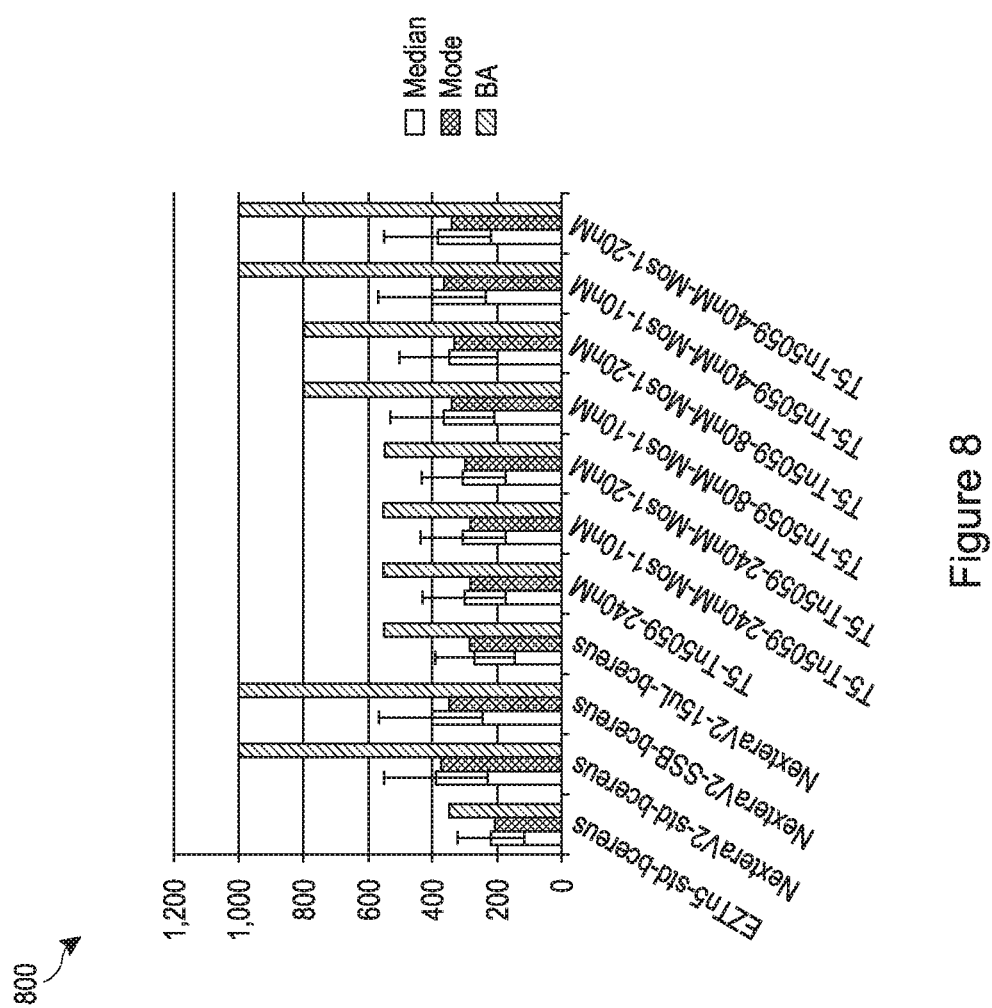
FIG. 8 shows a bar graph of insert size in the tagmented libraries of FIG. 7.
Figure 9:
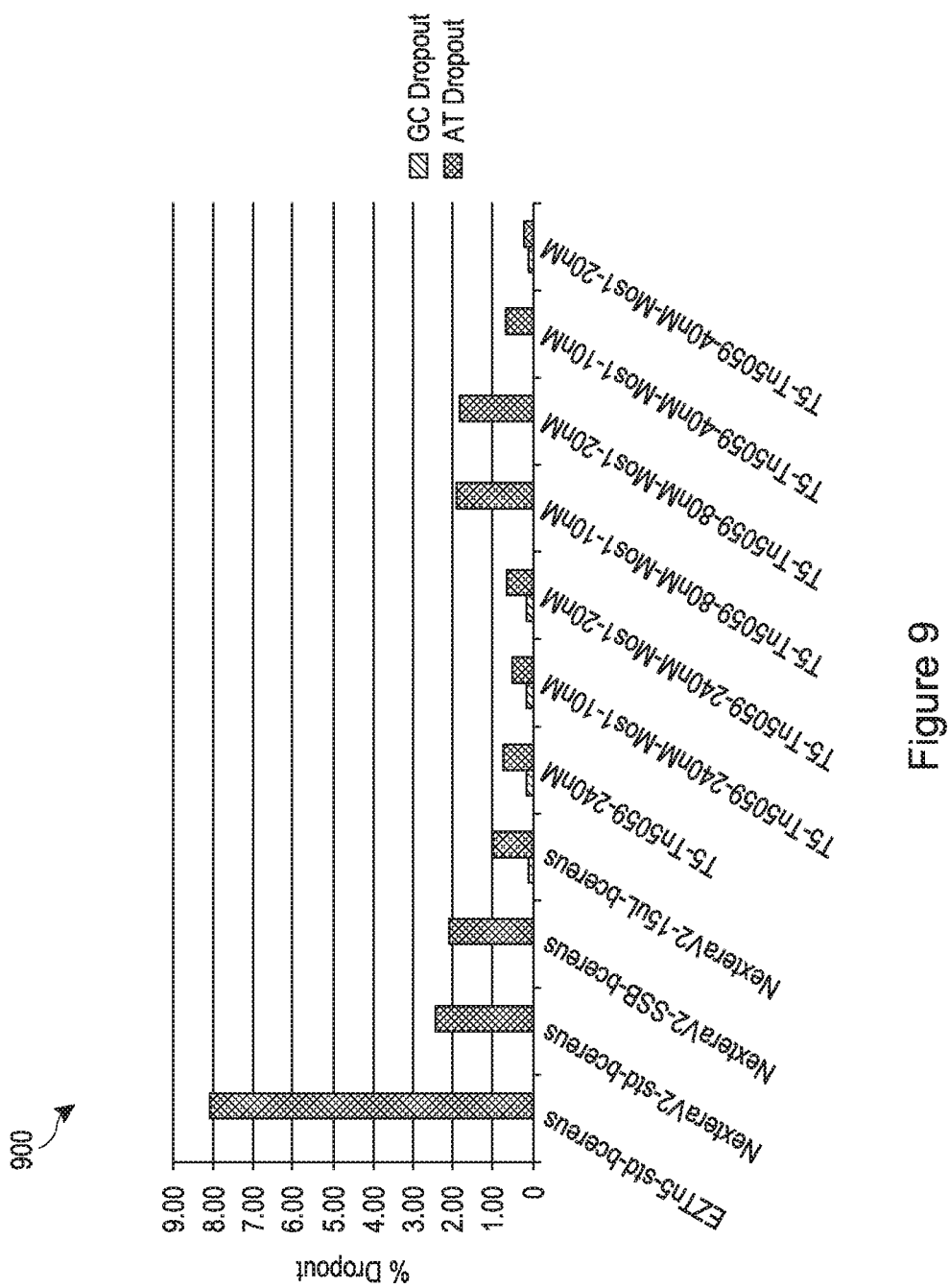
FIG. 9 shows a bar graph of the percent AT dropout and the percent GC dropout in the tagmented libraries of FIG. 7.
Figure 10:
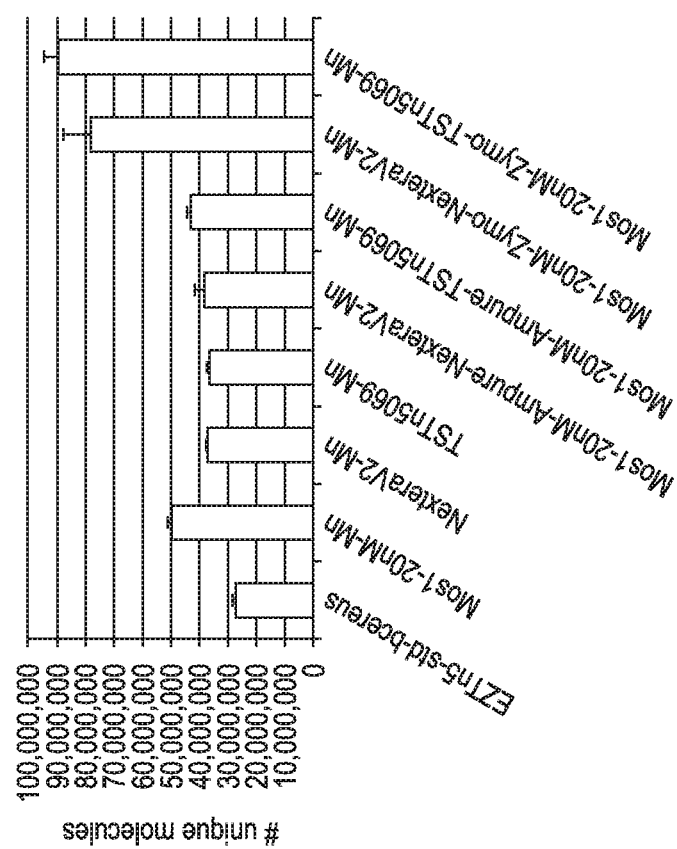
FIG. 10 shows a plot of the number of unique molecules in Mos1+Tn5 sequentially tagmented DNA libraries.
Figure 11:
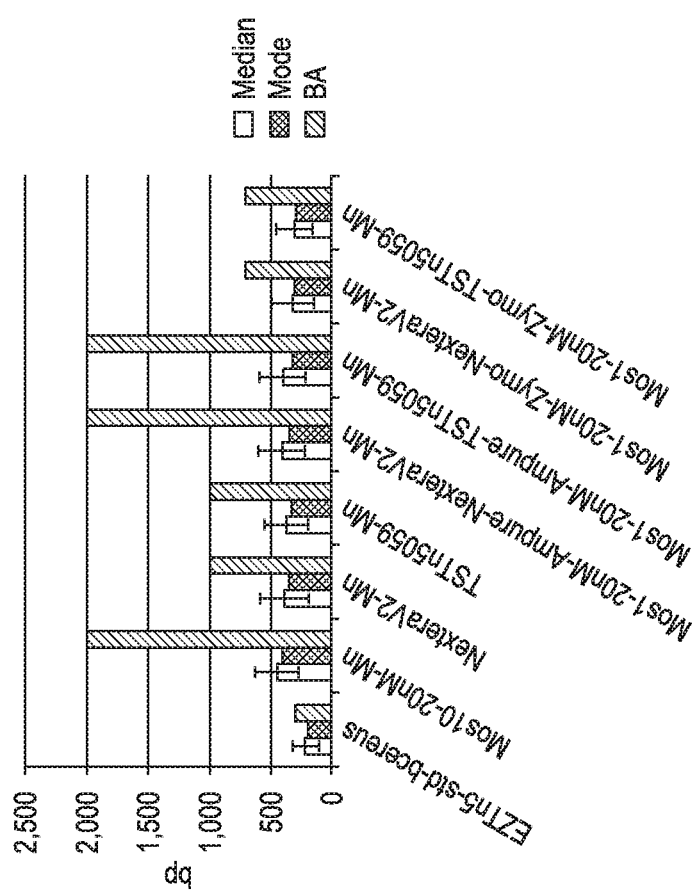
FIG. 11 shows a plot of the insert size in the tagmented libraries of FIG. 10.
Figure 12:
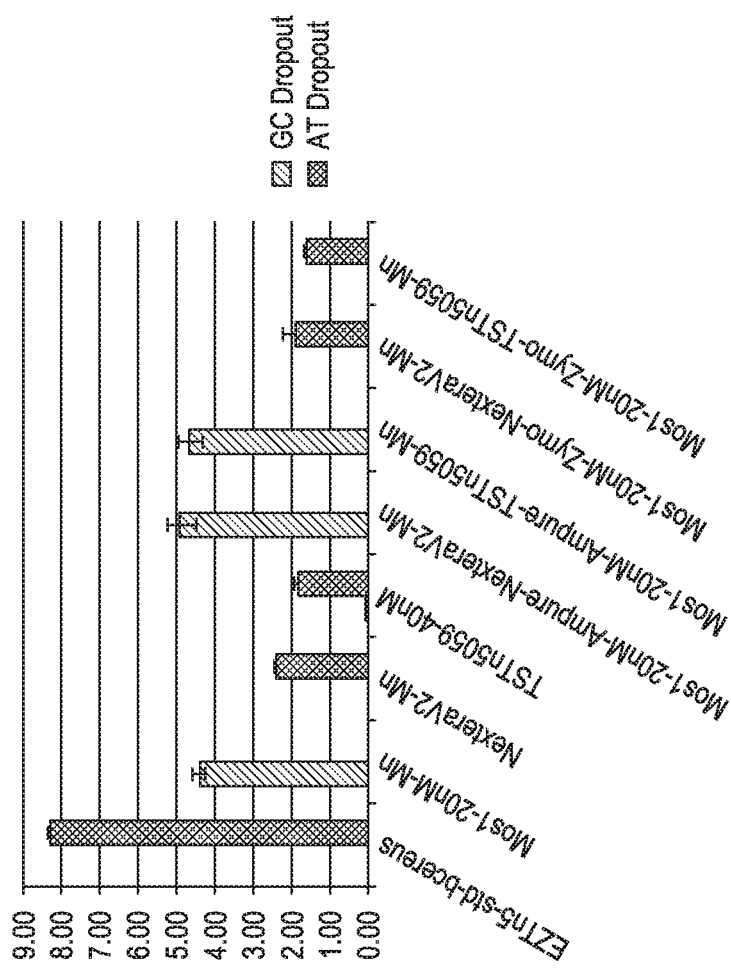
FIG. 12 shows a plot of the percent AT dropout and the percent GC dropout in the tagmented libraries of FIG. 10.
Figure 13:
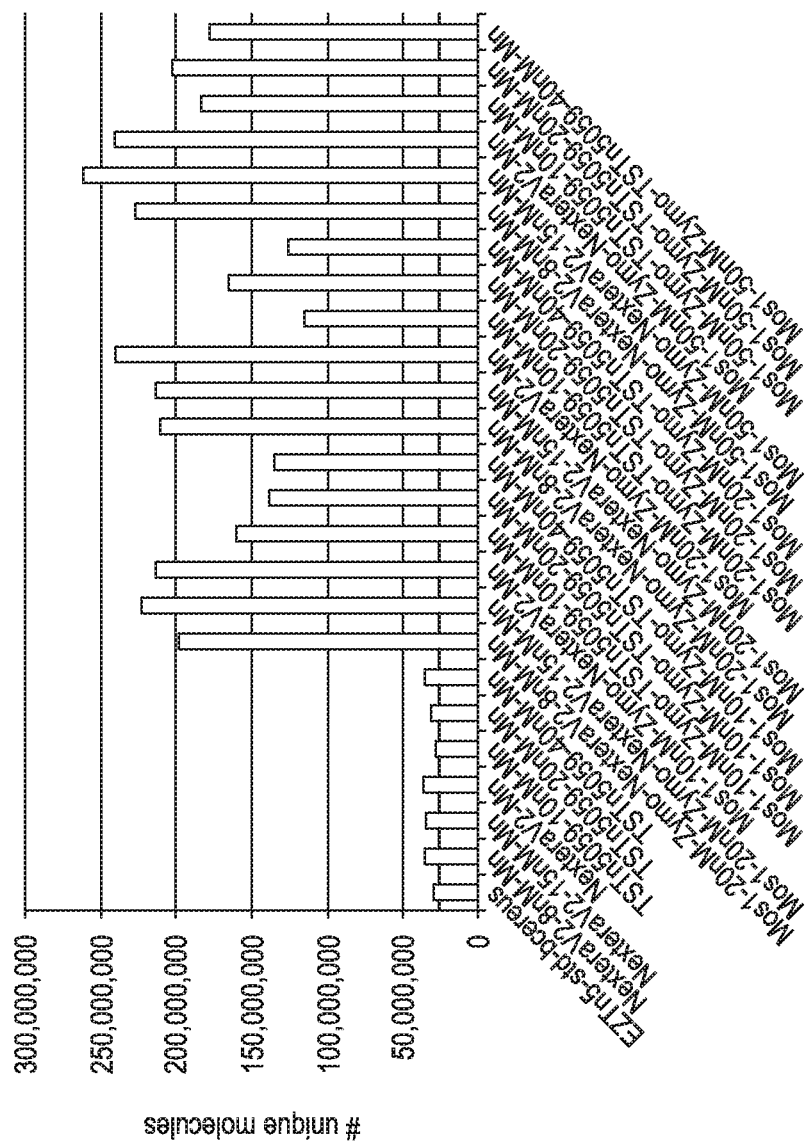
FIG. 13 shows a bar graph of the number of unique molecules in Mos1+Tn5 tagmented DNA libraries prepared using different concentrations of transposomes.
Figure 14:
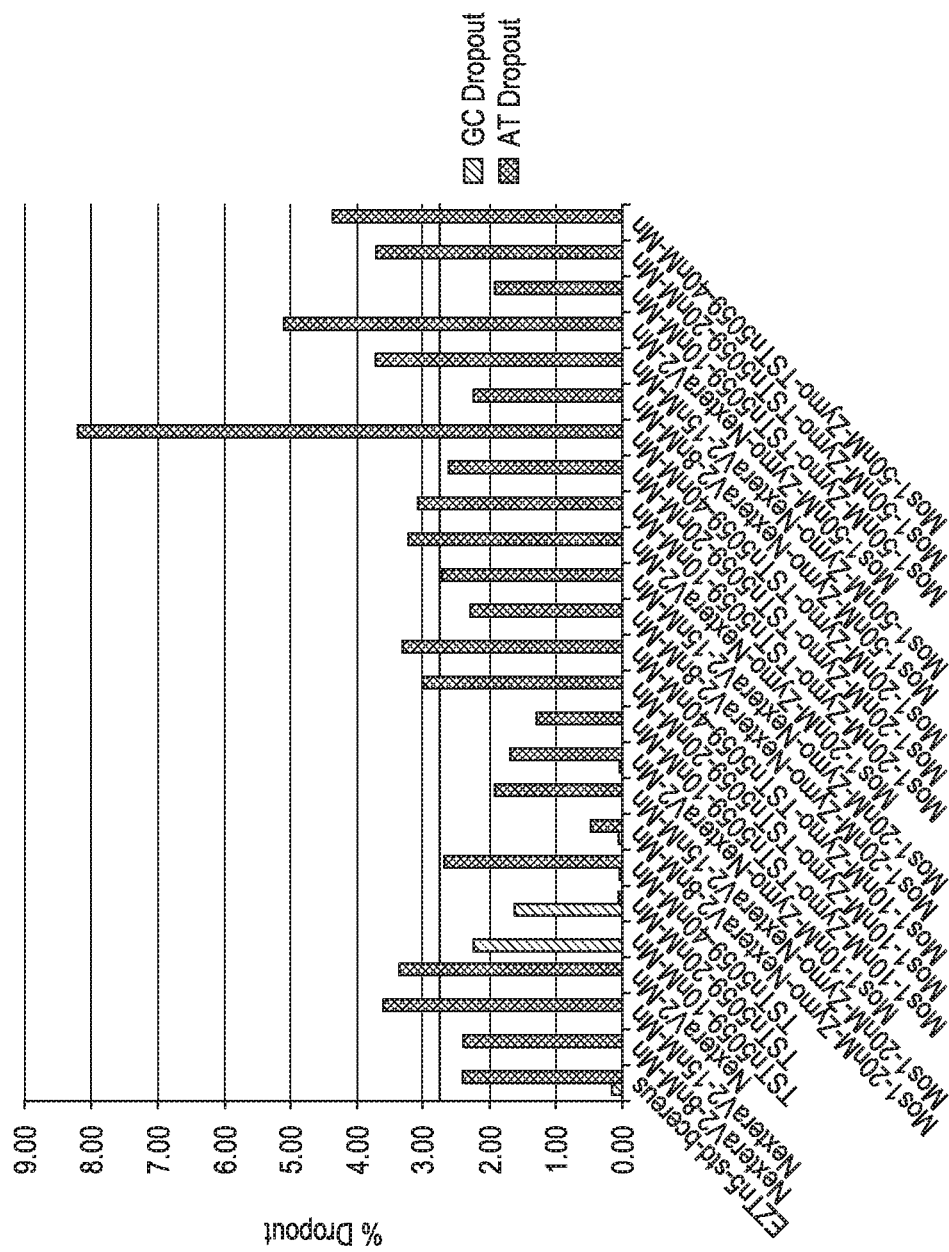
FIG. 14 shows a bar graph of the percent AT dropout and the percent GC dropout in the tagmented libraries of FIG. 13.

FIG. 8 shows a bar graph 800 of insert size in the tagmented libraries of FIG. 7. This graph shows the effect of Mos1 concentration to the final insert sizes. A Mos1 concentration of the range 10-20 nM does not have a major impact on the insert sizes. FIG. 9 shows a bar graph 900 of the percent AT dropout and the percent GC dropout in the tagmented libraries of FIG. 7. The data show that in general the libraries prepared using sequential tagmentation there is a substantial decrease in the percent AT dropout and a slight increase in the percent GC dropout compared to the NexteraV2 control libraries. For example, the percent AT dropout in the TS-Tn5059-40 nM-Mos1-20 nM is substantially decreased and the percent GC dropout slightly increased compared to the NexteraV2-std-bcereus library.

Example 2

Generating Sequencing Library with Mu Transposome Complex

Figure 15:
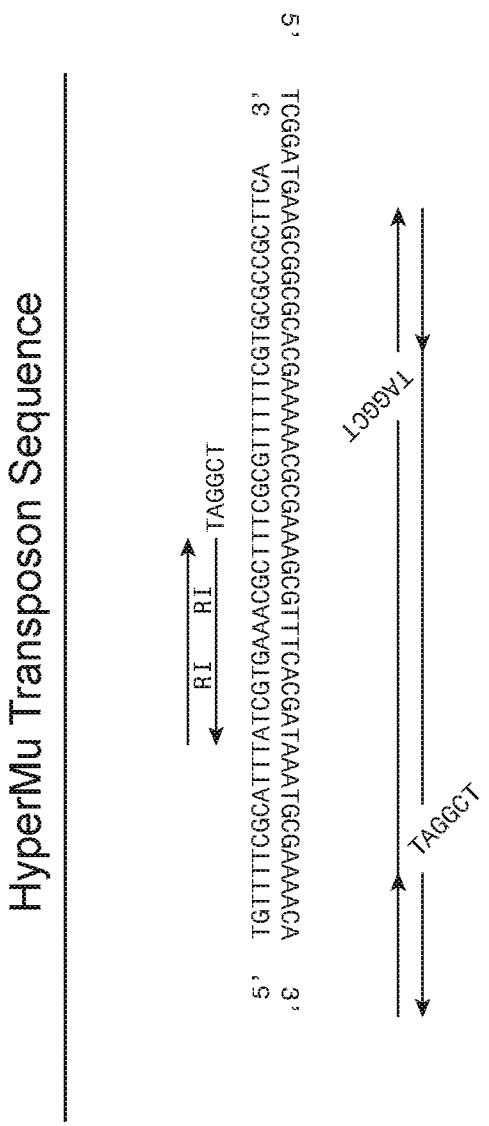
FIG. 15 shows HyperMu™ transposon sequence (SEQ ID NO:01, and SEQ ID NO:02).

HyperMu™ (Epicentre, Madison, Wis.), a mutant Mu transposase is used to generate sequencing library. HyperMu™ Transposase, a hyperactive enzyme that retains the highly random insertion characteristics of MuA transposase but is at least 50-times more active in vitro than the enzyme available from other suppliers. Upon Mu transposition, the transposon arms (i.e. RI and R11) together with any attached sequence would be transferred to the template DNA, at the same time fragmenting the template. HyperMu™ transposon sequence and the primer sequences are shown in FIG. 15-16. The Tn5 enzyme used was EZTn5, Tn5 from Nextera V2 kit.

Assessing Activity of Mu Transposome

Figure 17:
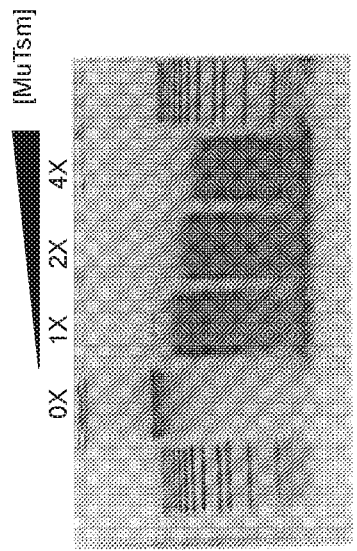
FIG. 17 shows the agarose gel electrophoresis analysis of the fragmentation products of bacteriophage genome at varying concentrations of HyperMu™ transposome.

The tagmentation capacity of HyperMu™ transposome is assessed on a ~50 kb bacteriophage genome. The tagmentation reaction was carried out in TA buffer for one hour at 37° C. at increasing concentration of HyperMu™ transposome. The fragmentation products were analyzed by agarose gel electrophoresis and the results are shown in FIG. 17.

Figure 18:
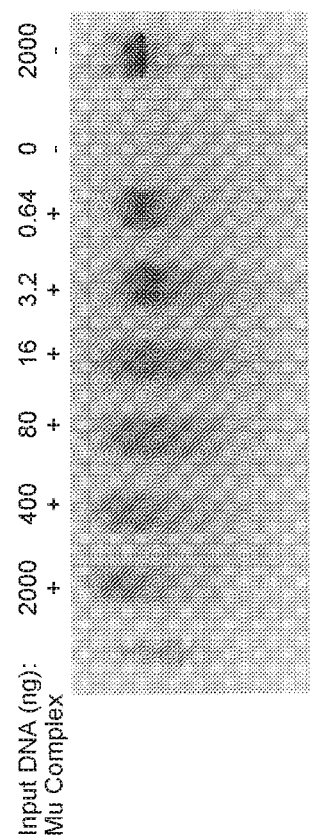
FIG. 18 shows the agarose gel electrophoresis analysis of the PCR amplified products of tagmented *E. Coli* chromosome after tagmentation with HyperMu™ transposome.

The HyperMu™ complexes were used to tagment E. coli chromosome and the tagmented fragments were amplified to introduce sequencing adapters. 25 cycles of PCR were carried out using P5-MUTS and P7-MUTS primers. The PCR products are analyzed by agarose gel electrophoresis and shown in FIG. 18. PCR products were observed with different amounts of input DNA.

Analysis of PCR Amplified Tagmented DNA

Figure 20:
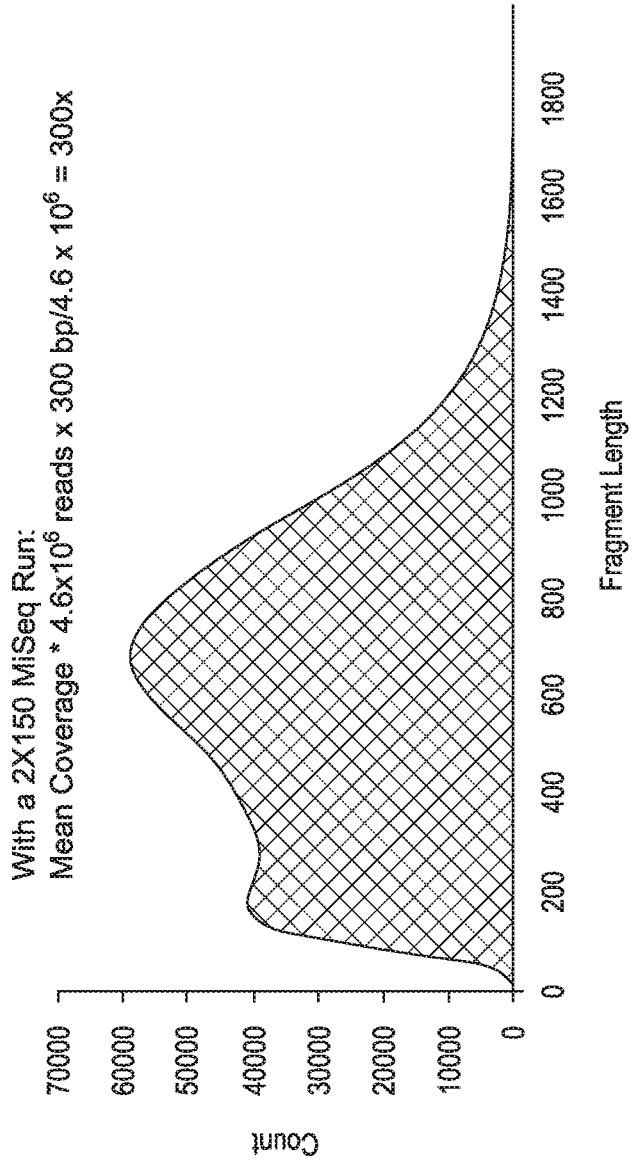
FIG. 20 shows the fragment length distribution after tagmentation of *E. Coli* chromosome using HyperMu™.

A 3.2 ng DNA was used for paired end sequencing on GAIIX (2×35 bp). The sample was sequenced on a single lane on GA. The total number of reads was 30,071,951 and number of unique reads <2000 bp was 4,599,874. The statistics of the sequencing run is shown in FIG. 19. The average size of the fragments sequenced was much longer than Nextera, and was close to 800 bp as shown in FIG. 20.

Figure 21:
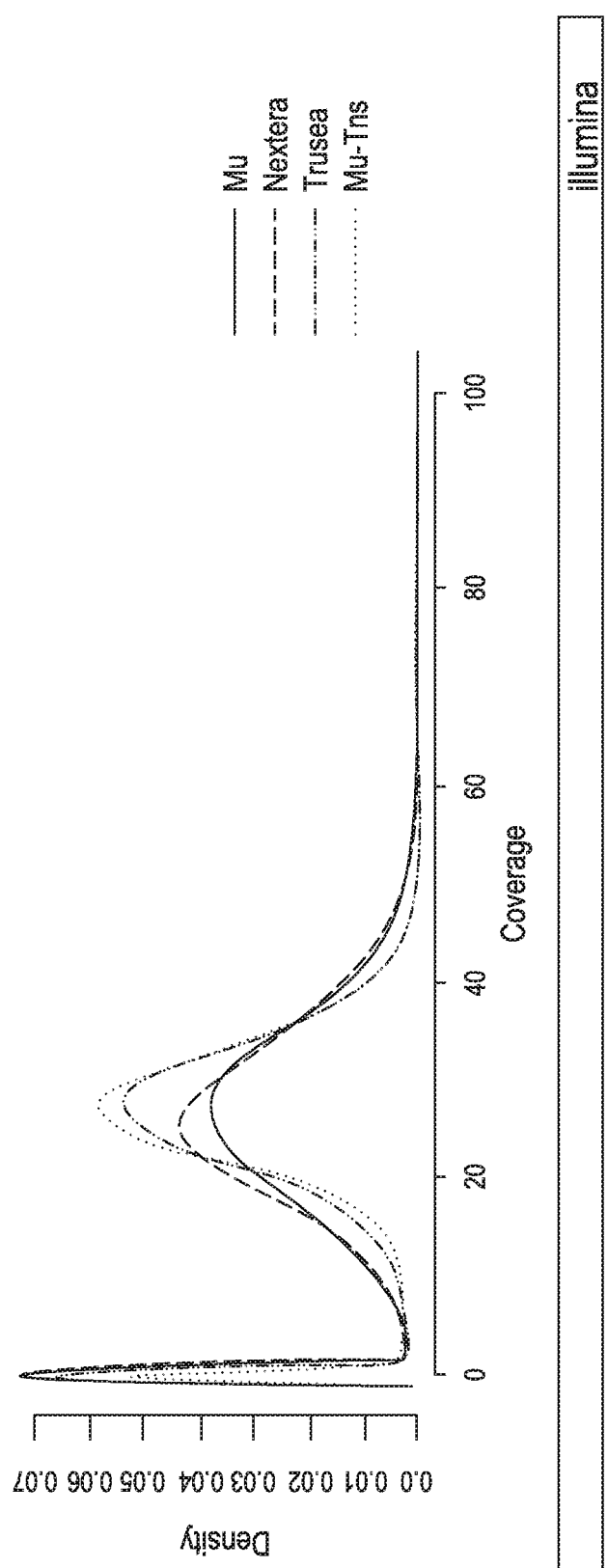
FIG. 21 shows the uniformity of coverage of Tn5 alone, HyperMu™ alone, TrueSeq alone, or a combination of HyperMu™ and Tn5.
Figure 22A:
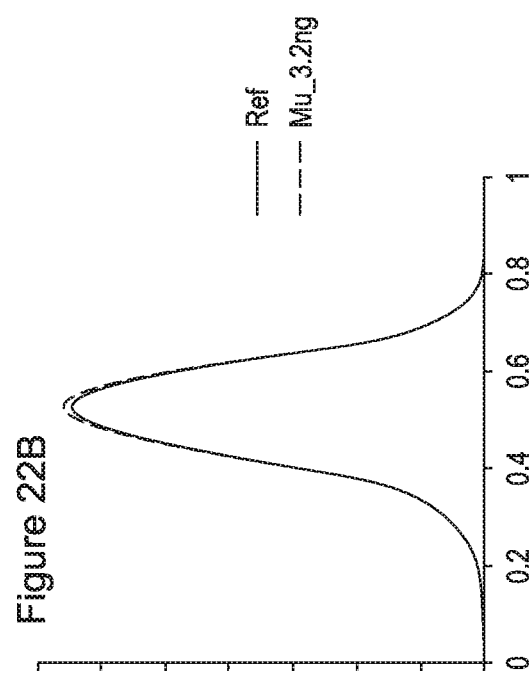
FIG. 22A is a comparison of the reference with tagmentation results using 3.2 ng of HyperMu™.
Figure 22B:
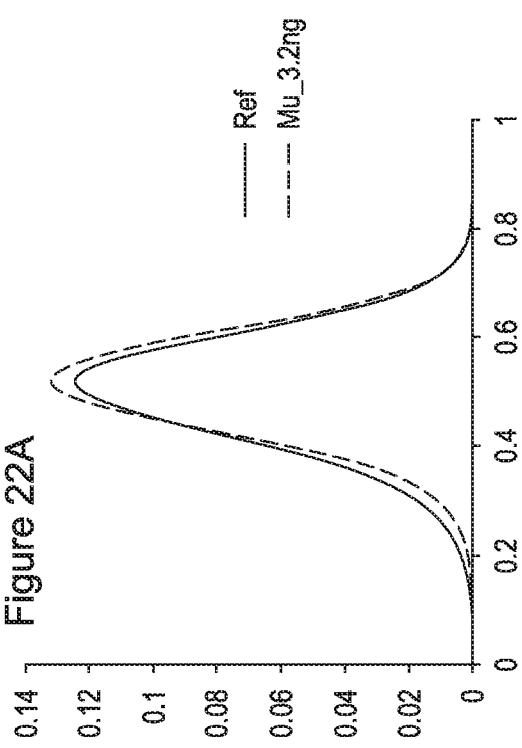
FIG. 22B is a comparison of the reference with tagmentation results using 1 ng of Nextera (Tn5) and 3.2 ng of HyperMu™.
Figure 22C:
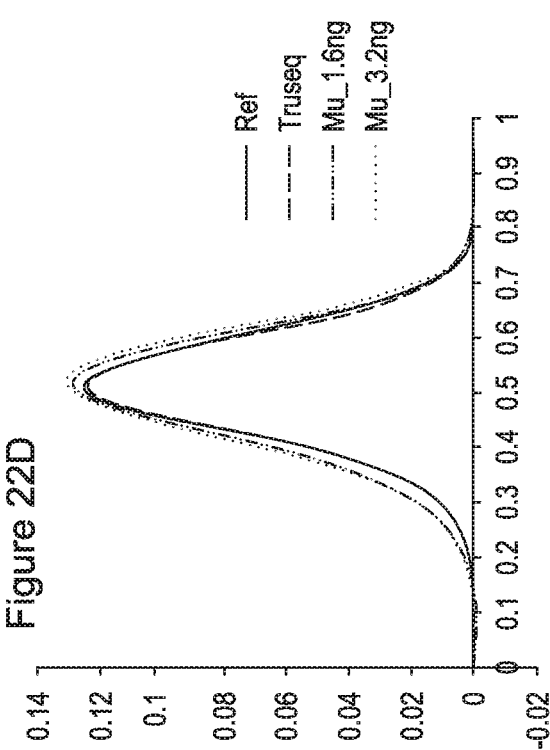
FIG. 22C is a comparison of the reference with TruSeq method.
Figure 22D:
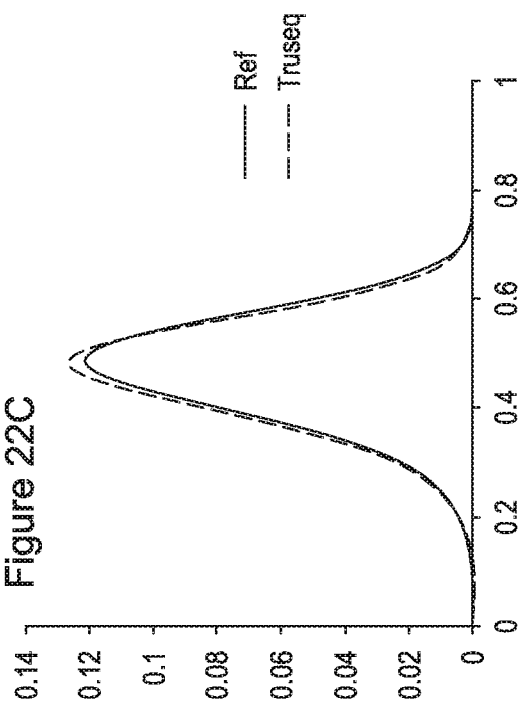
FIG. 22D is a comparison of the reference with Truseq method, tagmentation with Nextera and HyperMu™.

The uniformity of the sequencing run was better for HyperMu™ compared to Tn5. The uniformity of the sequencing run was better for HyperMu™ with Tn5 as compared to HyperMu™ or Tn5 alone. The uniformity of the sequencing run was comparable to TruSeq. The results are shown in FIG. 21. The observed GC bias for HyperMu™ is similar to Tn5 and shown in FIG. 22.

The experiments set forth in FIGS. 1-5 were performed to characterize the effect of Tn5 tagmentation buffer composition and reaction conditions on library output and sequencing metrics. In particular, in experiments set forth in FIGS. 1-3, Mos-1 was added to Tn5 tagmentation reactions. The Tn5 enzyme used was EZTn5, Tn5 from Nextera V2 kit, or mutant TS-Tn5059.

In experiments set forth in FIGS. 4 and 5, Mos-1 tagmentation reaction was performed first, and the tagmented DNA was washed to remove tagmentation buffer from the first reaction. Subsequently, the tagmented DNA was further tagmented using a Tn5 enzyme (EZTn5, Tn5 from Nextera V2 kit, or mutant TS-Tn5059). Various wash methods tested included Ampure beads and Zymo Clean and Concentrator kit (Zymo).

To evaluate the effect of tagmentation buffer composition and reaction conditions on library output and sequencing metrics, Tn5 tagmented DNA libraries were constructed using Bacillus cereus genomic DNA. Each tagmented library was prepared using 25 ng input of B. cereus genomic DNA. The genomic content of B. cereus is about 40% GC and about 60% AT.

Tagmentation buffers were prepared as 2× formulations. For each library, a tagmentation reaction was performed by mixing 20 µL B. cereus genomic DNA (25 ng), 25 µL 2× tagmentation buffer, and 5 µL enzyme (10×Ts-Tn5059 or 10×Ts-Tn5) in a total reaction volume of 50 µL. Reactions were incubated at 55° C. for 5 minutes. Following the tagmentation reaction, the samples were processed according to the standard Nextera™ sample preparation protocol. Libraries were sequenced using Illumina's SBS (sequencing-by-synthesis) chemistry on a MiSeq device. Sequencing runs were 2×71 cycles using a V2 MiSeq kit. Fragment size distribution in each library was evaluated on a Bioanalyzer.

Example 3

Tn5 and Mos1 Sequential Tagmentation in Solution

Tn5 transposases have decreased activity in buffers that contain >50 mM NaCl and Mos1 transposases have decreased activity in buffers that contain <150 mM NaCl. A sequential tagmentation to optimize the activity of both enzyme can be carried out.

Tn5 Tagmentation Followed by Mos1 Tagmentation

Standard Nextera™ (Epicentre, Madison, Wis.) tagmentation using conditions and buffers specified in the Nextera library prep protocols are used. After the initial Tn5 tagmentation, the reaction temperature is reduced to <30° C. Concentrated NaCl is then added to the reaction to a final concentration of 150-300 mM. Mos1 transposome is then added to the tagmentation reaction and the reaction is incubated at 30° C. Once tagmentation is complete, the reaction is cleaned-up either using Ampure™ beads (Beckman Coulter, CA, USA) or Zymo Clean & Concentrator™ cartridges (Zymo Research, Irvine, Calif.). The remaining protocol for adaptor addition through PCR and final clean-up and size selection is specified in the Nextera™ library prep protocol.

Mos1 Tagmentation Followed by Clean-Up to Remove the High Salt Buffer, Followed by Tn5 Tagmentation Standard Nextera™ (Epicentre, Madison, Wis.) buffers are used with the inclusion of 150-300 mM NaCl for Mos1 optimal activity. Mos1 is then added to the reaction and incubated at 30° C. Post tagmentation, the reaction is cleaned-up using Ampure™ beads (Beckman Coulter, CA, USA) or Zymo Clean & Concentrator™ cartridges (Zymo Research, Irvine, Calif.), or similar methods for DNA purification. The cleaned-up fragmented DNA material is then used as the DNA input for the secondary tagmentation using Tn5 or Tn5 mutant transposomes. After the second tagmentation, the reaction is cleaned-up either using Ampure™ beads (Beckman Coulter, CA, USA) or Zymo Clean & Concentrator™ cartridges (Zymo Research, Irvine, Calif.), or similar methods. The remaining protocol for adaptor addition through PCR and final clean-up and size selection is specified in the Nextera™ library prep protocol (Epicentre, Madison, Wis.).

Mos1 Tagmentation Followed by a Dilution to Reduce the High Salt Buffer, Followed by Tn5 Tagmentation Standard Nextera™ buffers (Epicentre, Madison, Wis.) are used with the inclusion of 150-300 mM NaCl for Mos1 optimal activity. Mos1 is then added to the reaction and incubated at 30° C. Post tagmentation, the reaction is diluted with reaction buffer to reduce the NaCl concentration to <50 mM. Tn5 is then added to the tagmentation reaction and incubated at <55° C. After the second tagmentation, the reaction is clean-up either using Ampure™ beads (Beckman Coulter, CA, USA) or Zymo Clean & Concentrator™ cartridges (Zymo Research, Irvine, Calif.), or similar DNA purification methods. The remaining protocol for adaptor addition through PCR and final clean-up and size selection is specified in the Nextera library prep Protocol™ (Epicentre, Madison, Wis.).

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of sequential tagmentation comprising:
   (a) providing a first transposome comprising a first transposon and a Mos-1 transposase, wherein the first transposome has a first tagmentation profile;
   (b) combining a target nucleic acid with the first transposome under conditions suitable for tagmentation, thereby generating a first tagmented nucleic acid; and
   (c) combining the first tagmented nucleic acid with a second transposome under conditions suitable for tagmentation, wherein the second transposome comprises a second transposon and a Tn5 transposase, wherein the second transposome has a second tagmentation profile different from the first tagmentation profile, thereby generating a second tagmented nucleic acid,
   wherein a reaction buffer used in step (b) is diluted to permit a tagmentation reaction with the second transposome.

2. The method of claim 1, wherein the first transposase and the second transposase have different insertion biases.

3. The method of claim 1, wherein step (c) comprises adding the second transposome to a reaction mixture comprising the first transposome.

4. The method of claim 3, wherein the first transposase remains bound to the first tagmented nucleic acid during the combining the first tagmented nucleic acid with a second transposome.

5. The method of claim 1, wherein the first transposon of the first transposome comprises a first adaptor and the second transposon of the second transposome comprises a second adaptor.

6. The method of claim 5, wherein the first and second adaptors comprise a sequence selected from the group consisting of barcodes, primer binding sequences, restriction endonuclease sites, and unique molecular indices.

7. The method of claim 1, wherein the first, second or both transposomes are immobilized on solid supports.

8. The method of claim 7, wherein the solid support comprises a bead.

9. The method of claim 1, further comprising: amplifying the second tagmented nucleic acid, thereby creating a sequencing library.

10. The method of claim 1, wherein a salt concentration of the reaction buffer is adjusted to permit tagmentation with the second transposome.

11. The method of claim 1, wherein the first transposon comprises a Mos-1 transposon, and the second transposon comprises a Tn5 transposon.

12. A method of sequential tagmentation comprising:
    (a) providing a first transposome comprising a first transposon and a Mos-1 transposase, and a second transposome comprising a second transposon and a Tn5 transposase;
    (b) combining a target nucleic acid with the first transposome in a reaction buffer under conditions suitable for tagmentation, thereby generating a first tagmented nucleic acid; and
    (c) combining the first tagmented nucleic acid with the second transposome under conditions suitable for tagmentation, wherein the reaction buffer is diluted to permit tagmentation with the second transposome, thereby generating a second tagmented nucleic acid.

13. The method of claim 12, wherein a salt concentration of the reaction buffer is adjusted to permit tagmentation with the second transposome.

14. The method of claim 12, wherein the first transposon comprises a Mos-1 transposon, and the second transposon comprises a Tn5 transposon.

* * * * *